United States Patent
Matier et al.

(10) Patent No.: US 7,825,134 B2
(45) Date of Patent: *Nov. 2, 2010

(54) AMELIORATION OF CATARACTS, MACULAR DEGENERATION AND OTHER OPHTHALMIC DISEASES

(75) Inventors: William L. Matier, Hockessin, DE (US); Ghanshyam Patil, Lincoln University, PA (US)

(73) Assignee: Othera Holding, Inc., Wilmington, DE (US)

( * ) Notice: Subject to any disclaimer, the term of this patent is extended or adjusted under 35 U.S.C. 154(b) by 1490 days.

This patent is subject to a terminal disclaimer.

(21) Appl. No.: 10/994,712

(22) Filed: Nov. 22, 2004

(65) Prior Publication Data

US 2005/0131025 A1 Jun. 16, 2005

Related U.S. Application Data

(63) Continuation-in-part of application No. 10/440,583, filed on May 19, 2003, now Pat. No. 7,442,711.

(60) Provisional application No. 60/523,803, filed on Nov. 20, 2003.

(51) Int. Cl.
*A61K 31/445* (2006.01)
*A61K 9/00* (2006.01)

(52) U.S. Cl. .................. 514/315; 424/400
(58) Field of Classification Search ........... 514/315; 424/400
See application file for complete search history.

(56) References Cited

U.S. PATENT DOCUMENTS

| | | | |
|---|---|---|---|
| 3,936,456 A | 2/1976 | Ramey et al. | 260/268 DK |
| 4,014,335 A | 3/1977 | Arnold | 128/260 |
| 4,287,175 A | 9/1981 | Katz | 424/78 |

(Continued)

FOREIGN PATENT DOCUMENTS

CA 2029402 5/1991

(Continued)

OTHER PUBLICATIONS

Barbarin, F., et al., "L'effet gem effect: measurement of interfunctional distance by electron paramagnetic resonance," *Nouv. J. Chim.*, 1980, 4(7), 437-444 (English Abstract).

(Continued)

*Primary Examiner*—Shengjun Wang
(74) *Attorney, Agent, or Firm*—Woodcock Washburn LLP

(57) ABSTRACT

Ophthalmically acceptable compositions used in arresting the development of macular degeneration, retinopathy, glaucoma, eyelid disorders, corneal disease, or uveitis are disclosed. The compositions comprise a pharmaceutically acceptable carrier or diluent and at least one compound having the formula:

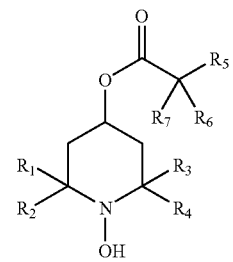

wherein $R_1$, $R_2$, $R_3$, $R_4$, $R_5$, $R_6$, and $R_7$ are as defined herein.

28 Claims, 4 Drawing Sheets

Bioavailability after dosing with compound 1 and tempol-H

U.S. PATENT DOCUMENTS

| | | | |
|---|---|---|---|
| 4,343,787 A | 8/1982 | Katz | 424/78 |
| 4,404,302 A | 9/1983 | Gupta et al. | 524/100 |
| 4,615,697 A | 10/1986 | Robinson | 604/890 |
| 4,691,015 A | 9/1987 | Behrens et al. | 544/198 |
| 4,804,539 A | 2/1989 | Guo et al. | 424/450 |
| 4,818,537 A | 4/1989 | Guo | 424/427 |
| 4,851,436 A | 7/1989 | Hoffman et al. | 514/529 |
| 4,871,742 A * | 10/1989 | Bonne et al. | 514/263.3 |
| 4,883,658 A | 11/1989 | Holly | 424/80 |
| 4,914,088 A | 4/1990 | Glonek et al. | 514/76 |
| 4,927,891 A | 5/1990 | Kamath et al. | 525/327.3 |
| 4,983,392 A | 1/1991 | Robinson | 424/427 |
| 5,004,770 A | 4/1991 | Cortolano et al. | 524/99 |
| 5,075,104 A | 12/1991 | Gressel et al. | 424/78.04 |
| 5,145,893 A | 9/1992 | Galbo et al. | 524/99 |
| 5,188,928 A | 2/1993 | Karino et al. | 430/513 |
| 5,209,927 A | 5/1993 | Gressel et al. | 424/78.04 |
| 5,225,196 A | 7/1993 | Robinson | 424/427 |
| 5,278,151 A | 1/1994 | Korb et al. | 514/76 |
| 5,294,607 A | 3/1994 | Glonek et al. | 514/76 |
| 5,399,473 A | 3/1995 | Shono et al. | 430/551 |
| 5,462,946 A | 10/1995 | Mitchell et al. | 514/315 |
| 5,466,233 A | 11/1995 | Weiner et al. | 604/890.1 |
| 5,475,013 A | 12/1995 | Talley et al. | 514/311 |
| 5,518,732 A | 5/1996 | Nigam | 424/427 |
| 5,578,586 A | 11/1996 | Glonek et al. | 514/76 |
| 5,707,643 A | 1/1998 | Ogura et al. | 424/428 |
| 5,718,922 A | 2/1998 | Herrero-Vanrell et al. | 424/501 |
| 5,869,079 A | 2/1999 | Wong et al. | 424/426 |
| 5,902,598 A | 5/1999 | Chen et al. | 424/423 |
| 5,981,548 A | 11/1999 | Paolini et al. | 514/316 |
| 5,981,584 A * | 11/1999 | Egbertson et al. | 514/534 |
| 6,001,853 A * | 12/1999 | Zigler et al. | 514/315 |
| 6,154,671 A | 11/2000 | Parel et al. | 604/20 |
| 6,251,090 B1 | 6/2001 | Avery et al. | 604/9 |
| 6,281,192 B1 | 8/2001 | Leahy et al. | 514/8 |
| 6,331,313 B1 | 12/2001 | Wong et al. | 424/427 |
| 6,375,972 B1 | 4/2002 | Guo et al. | 424/423 |
| 6,410,045 B1 | 6/2002 | Schultz et al. | 424/429 |
| 6,429,194 B1 | 8/2002 | Leahy et al. | 514/8 |
| 6,433,007 B1 | 8/2002 | Garner et al. | |
| 6,469,057 B1 * | 10/2002 | Lai | 514/492 |
| 2003/0109566 A1 | 6/2003 | Mano et al. | 514/407 |
| 2004/0002461 A1 | 1/2004 | Matier et al. | |

FOREIGN PATENT DOCUMENTS

| | | |
|---|---|---|
| CA | 2065796 | 10/1992 |
| DE | 38 01 790 A1 | 7/1989 |
| DE | 40 00 551 A1 | 7/1990 |
| DE | 42 00 192 A1 | 7/1992 |
| DE | 43 27 297 A1 | 2/1994 |
| DE | 44 11 369 A1 | 10/1994 |
| DE | 43 20 444 A1 | 12/1994 |
| DE | 44 24 706 A1 | 1/1995 |
| DE | 44 26 222 A1 | 3/1995 |
| DE | 196 16 185 A1 | 10/1996 |
| DE | 196 18 197 A1 | 11/1997 |
| DE | 198 16 681 A1 | 10/1998 |
| DE | 197 35 255 A1 | 2/1999 |
| EP | 0 138 767 B2 | 3/1988 |
| EP | 0 157 738 B1 | 4/1989 |
| EP | 0 378 054 A3 | 7/1990 |
| EP | 0 490 771 A1 | 6/1992 |
| EP | 0 356 677 B1 | 6/1993 |
| EP | 0 309 400 B1 | 3/1994 |
| EP | 0 352 221 B1 | 3/1994 |
| EP | 0 309 401 B2 | 10/1994 |
| EP | 0 627 428 A1 | 12/1994 |
| EP | 0 638 616 A1 | 2/1995 |
| EP | 0 467 850 B1 | 7/1995 |
| EP | 0 467 848 B1 | 1/1996 |
| EP | 195 30 468 A1 | 2/1997 |
| EP | 0 565 487 B1 | 4/1997 |
| EP | 0 588 763 B1 | 12/1997 |
| EP | 0 508 398 B1 | 7/1998 |
| EP | 0 601 745 B1 | 3/1999 |
| EP | 0 665 294 B1 | 5/1999 |
| EP | 0 644 195 B1 | 7/1999 |
| EP | 0 761 466 B1 | 8/1999 |
| EP | 0 775 684 B1 | 8/1999 |
| EP | 0 641 822 B1 | 12/1999 |
| EP | 0 745 646 B1 | 7/2001 |
| EP | 0 636 610 B1 | 3/2002 |
| EP | 0 943 665 B1 | 11/2003 |
| EP | 0 934 972 B1 | 4/2004 |
| GB | 2 253 411 A | 9/1992 |
| JP | 58-99449 | 6/1983 |
| JP | 63-85547 | 4/1988 |
| JP | 3-31342 | 2/1991 |
| JP | 9-52975 | 2/1997 |
| JP | 10-45777 | 2/1998 |
| JP | 10-45778 | 2/1998 |
| JP | 10-219140 | 8/1998 |
| JP | 10-220381 | 8/1998 |
| JP | 2000-327844 | 11/2000 |
| WO | WO 95/17900 A1 | 7/1995 |
| WO | WO 96/15110 | 5/1996 |
| WO | WO 96/37576 | 11/1996 |
| WO | WO 97/39051 | 10/1997 |
| WO | WO 97/39052 | 10/1997 |
| WO | WO 98/28256 A1 | 7/1998 |
| WO | WO 98/47893 A1 | 10/1998 |
| WO | WO 98/50360 A1 | 11/1998 |
| WO | WO 99/05108 A1 | 2/1999 |
| WO | WO 99/33911 A1 | 7/1999 |
| WO | WO 99/43666 A2 | 9/1999 |
| WO | WO 01/17738 A1 | 3/2001 |
| WO | WO 02/34262 A1 | 5/2002 |

OTHER PUBLICATIONS

Carlsson, D.J., et al., "Photostabilization ofpolypropylene by a hindered amine," *J. of Polym. Science: Polym. Letts. Ed.*, 1981, 19, 549-554.

Carlsson, D.J., et al., "Hindered amines as antioxidants in UV exposed polymers," *Polym. Science Technol. (Plenum)*, 1984, 26(*Polym. Addit.*), 35-47.

Chen, K., et al., "Oxidation of hydroxylamines to nitroxide spin labels in living cells," *Biochim. et Biophys. Acta*, 1988, 970, 270-277.

Chmela, Š., et al., "The influence of substituents on the photostabililizing efficiency of hindered amine stabilizers in polypropylene," *Polym. Degrad. & Stab.*, 1990, 27, 159-167.

Ciba-Geigy, A.-G., "NOR (Nitrogen-oxygen-R) hindered amine light stabilizers in polymeric microparticles," *Res. Discl.*, 1991, 323, 155-157 (English abstract).

Dragutan, I., et al., "New amino-nitroxide spin labels," *Bioorg. & Med. Chem.*, 1996, 4(10), 1577-1583.

Johnson, P.Y., et al., "The reformatsky reaction of ethyl α-bromo esters with Bis(chloromethyl) ether," *J. Org. Chem.*, 1973, 38(13), 2346-2350.

Klemchuk, P.P., et al., "Stabilization mechanisms of hindered amines," *Polym. Degrad. Stab.*, 1988, 22, 241-274.

Kokhanov, Y., et al., "Synthesis of some heterocyclic radicals of the iminoxyl class," *Khim. Geterotsikl. Soedin.*, 1971, 11, 1527-1529.

Kurosaki, T., et al., "Polymers having stable radicals. II. Synthesis of nitroxyl polymers from 4-methacryloyl derivatives of 1-hydroxy-2,2,6,6-tetramethylpiperidine," *J. of Polym. Sci.: Polym. Chem. Ed.*, 1974, 12, 1407-1420.

Litvin, E.F., et al., "Investigation of the stepwise mechanism of the hydrogenation of iminoyxl bi- and polyradicals of platinum and nickel catalysts," *Zh. Org. Kim.*, 1970, 6(12), 2365-2369.

Nethsinghe, L., et al., "Mechanisms of antioxidant action: complementary chain-breaking mechanisms in the mechanostabilization of rubbers," *Rubber Chem. & Technol.,* 1984, 57, 918-925.

Ohkatsu, Y., et al., "Inhibition of antoxidation by hindered amine light stabilizers and their derivatives," *Sekiyu Gakkaishi,* 1994, 37(4), 395-399.

Zahradnickova, A., et al., "Comparison of the stabilization ability of N-substituted hindered-amine light stabilizers in hydrocarbon model compounds and in polymers," *Plasty Kauc.,* 1987, 24(6), 174-177 (English abstract).

Age-Releated Eye Disease Study Research Group, AREDS Report No. 8, *Arch. Ophthalmol.,* 2001, 119, 1417-1436.

Ahmed, I., et al., "Physicochemical determinants of drug diffusion across the conjunctiva, sclera, and cornea," *J. of Pharm. Sci.,* 1987, 76(8), 583-586.

Ambati, J., et al., "Age-related macular degeneration: etiology, pathogenesis, and therapeutic strategies," *Survey of Ophthalmology,* 2003, 48(3), 257-293.

Augustin, A.J., et al, "Oxidative reactions in the tear fluid of patients suffering from dry eyes," *Graefe's Arch. Clin. Exp. Ophthalmol.,* 1995, 233, 694-698.

Berra, A., et al., "Age-related antioxidant capacity of the vitreous and its possible relationship with simultaneous changes in photoreceptors, retinal pigment epithelium and Brushs' membrane in human donors' eyes," *Arch. Gerontol. Geriatrics,* 2002, 34, 371-377.

Čejková, J., et al., "reactive oxygen species (ROS)-generating oxidases in the normal rabbit cornea and their involvement in the corneal damage evoked by UVB rays," *Histol and Histopathol,* 2001, 16, 523-533.

Foster, C.S., et al., "Efficacy of etanercept in preventing relapse of uveitis controlled by methotrexate," *Arch. Ophthalmol.,* 2003, 121, 437-440.

Harris, M.D., et al., "Laser eye injuries in military occupations," *Aviat. Space Environ. Med.,* 2003, 74(9), 947-952.

Hartwick, A.T.E., "Beyond intraocular pressure: neuroprotective strategies for future glaucoma therapy," *Optometry and Vision Science,* 2001, 78(2), 85-94.

Hayashi, S., et al., "Oxygen free radical damage in the cornea after excimer laser therapy," *Br. J. Ophthalmol.,* 1997, 81, 141-144.

Hosseini, K., et al., "Non-invasive monitoring of commonly used intraocular drugs against endophthalmitis by raman spectroscopy," *Lasers in Surg. Med.,* 2003, 32, 265-270.

Izzotti, A., et al., "Oxidative deoxyribonucleic damage in the eyes of glaucoma patients," *Am. J. Med.,* 2003, 114, 638-646.

Kasetsuwan, N., et al., "Effect of topical ascorbic acid on free radical tissue damage and inflammatory cell influx in the cornea after excimer laser corneal surgery," *Arch. Ophthalmol.,* 1999, 117, 649-652.

Lou, M.F., "Redox regulation in the lens," *Prog. Retinal & Eye Res.,* 2002, 22, 657-682.

McDonald, H.F., et al., "Operating microscope-induced retinal phototoxicity during pars plana vitrectomy," *Arch. Ophthalmol.,* 1988, 106, 521-523.

Moffat, B.A., et al., "Age-related changes in the kinetics of water transport in normal human lenses," *Exp. Eye Res.,* 1999, 69, 663-669.

Moritera, T., et al., "Microspheres of biodegradable polymers as a drug-delivery system in the vitreous," *Invest. Ophthalmol. Vis. Sci.,* 1991, 32(6), 1785-1790.

Osborne, N.N., et al., "Some current ideas on the pathogenesis and the role of neuroprotection in glaucomatous optic neuropathy," *Eur. J. Ophthalmol.,* 2003, 13(*Suppl. 3*), S19-S26.

Pavilack, M.A., et al., "Site of potential operating microscope light-induced phototoxicity on the human retina during temporal approach eye surgery," *Ophthalmol.,* 2001, 108(2), 381-385.

Stone, D.U., et al., "Ocular rosacea: an update on pathogenesis and therapy," *Curr. Opin. Ophthalmol.,* 2004, 15(6), 499-502.

Wein, F.B., et al., "Current understanding of neuroprotection in glaucoma," *Curr. Op. Ophthalmol.,* 2002, 13, 61-67.

Zamir, E., et al., "Nitroxide stable radical suppresses autoimmune uveitis in rats," *Free Rad. Biol. Med.,* 1999, 27, 7-15.

\* cited by examiner

Bioavailability after dosing with compound 1 and tempol-H

AMELIORATION OF CATARACTS, MACULAR DEGENERATION AND OTHER OPHTHALMIC DISEASES

CROSS-REFERENCE TO RELATED APPLICATIONS

Continuation-in-part of U.S. application Ser. No. 10/440,583, filed May 19, 2003 now U.S. Pat. No. 7,442,711, also claiming benefit of U.S. Provisional Application No. 60/523,803, filed Nov. 20, 2003, the entire contents of each of which are incorporated by reference herein.

FIELD OF THE INVENTION

The present invention is directed to compositions that ameliorate the development of cataracts in the eye of a patient and to methods for effecting such amelioration. In preferred embodiments of the invention, cataract development or growth is essentially halted. The present invention is also directed to the treatment of macular degeneration in the eye and to certain other uses. In accordance with preferred embodiments, the compositions of this invention are capable of administration to patients without the need for injections and can be formulated into eye drops for such administration. Methods for treatment of cataracts and macular degeneration are also provided, as are methods for the preparation of the novel compounds and compositions useful in the practice of the invention.

BACKGROUND OF THE INVENTION

Various patents and other publications are referenced herein. The contents of each of these patents and publications are incorporated by reference herein, in their entireties. The entire contents of commonly-owned co-pending U.S. application Ser. No. 10/440,583, filed May 19, 2003, are incorporated by reference herein.

Aging-related cataract results from gradual opacification of the crystalline lens of the eye. This disease is presently treated by surgical removal and replacement of the affected lens. It is believed that once begun, cataract development proceeds via one or more common pathways that culminate in damage to lens fibers. This condition progresses slowly and occurs predominantly in the elderly. Alternatively, cataract may form because of surgical, radiation or drug treatment of a patient, e.g. after surgery of an eye to repair retinal damage (vitrectomy) or to reduce elevated intraocular pressure; x-irradiation of a tumor; or steroid drug treatment. A significant retardation of the rate of cataract development in such patients may eliminate the need for many surgical cataract extractions. This reduction would provide tremendous benefits both to individual patients and to the public health system.

A less serious but more pervasive condition of the ocular lens is presbyopia. The lens is enveloped by a tough collagen capsule that is thought to impart elasticity to the lens, enabling it to focus at different distances through ciliary muscle-controlled changes of curvature. As the lens ages, it increases in volume and hence progressively loses its elasticity, which diminishes an individual's ability to focus on near objects. This condition is known as presbyopia, and occurs in a large percentage of the aging population.

In addition to cataract and presbyopia, the eye can experience numerous diseases and other deleterious conditions that affect its ability to function normally. Many such conditions can be found in the interior and most particularly at the rear of the eye, where lies the optic nerve and the retina, seven layers of alternating cells and processes that convert a light signal into a neural signal. Diseases and degenerative conditions of the optic nerve and retina are the leading causes of blindness throughout the world.

A significant degenerative condition of the retina is macular degeneration, also referred to as age-related macular degeneration (AMD). AMD is the most common cause of vision loss in the United States in those 50 or older, and its prevalence increases with age. AMD is classified as either wet (neovascular) or dry (non-neovascular). The dry form of the disease is most common. It occurs when the central retina has become distorted, pigmented, or most commonly, thinned. The wet form of the disease is responsible for most severe loss of vision. The wet form of macular degeneration is usually associated with aging, but other diseases that can cause wet macular degeneration include severe myopia and some intraocular infections like histoplasmosis, which may be exacerbated in individuals with AIDS. A variety of elements may contribute to macular degeneration, including genetic makeup, age, nutrition, smoking and exposure to sunlight.

Retinopathy associated with diabetes is a leading cause of blindness in type 1 diabetes, and is also common in type 2 diabetes. The degree of retinopathy depends on the duration of the diabetes, and generally begins to occur ten or more years after onset of diabetes. Diabetic retinopathy may be classified as (1) non-proliferative or background retinopathy, characterized by increased capillary permeability, edema, hemorrhage, microaneurysms, and exudates, or 2) proliferative retinopathy, characterized by neovascularization extending from the retina to the vitreous, scarring, fibrous tissue formation, and potential for retinal detachment. Diabetic retinopathy is believed to be caused, at least in part, by the development of glycosylated proteins due to high blood glucose. Glycosylated proteins generate free radicals, resulting in oxidative tissue damage and depletion of cellular reactive oxygen species (ROS) scavengers, such as glutathione.

Several other less common, but nonetheless debilitating retinopathies include choroidal neovascular membrane (CNVM), cystoid macular edema (CME, also referred to as macular edema or macular swelling), epi-retinal membrane (ERM) (macular pucker) and macular hole. In CNVM, abnormal blood vessels stemming from the choroid grow up through the retinal layers. The fragile new vessels break easily, causing blood and fluid to pool within the layers of the retina. In CME, which can occur as a result of disease, injury or surgery, fluid collects within the layers of the macula, causing blurred, distorted central vision. ERM (macular pucker) is a cellophane-like membrane that forms over the macula, affecting the central vision by causing blur and distortion. As it progresses, the traction of the membrane on the macula may cause swelling. ERM is seen most often in people over 75 years of age. Its etiology is unknown, but may be associated with diabetic retinopathy, posterior vitreous detachment, retinal detachment or trauma, among other conditions.

Another disease of the interior of the eye is uveitis, or inflammation of the uveal tract. The uveal tract (uvea) is composed of the iris, ciliary body, and choroid. The uvea is the intermediate of the three coats of the eyeball, sandwiched between the sclera and the retina in its posterior (choroid) portion. Uveitis may be caused by trauma, infection or surgery, and can affect any age group. Uveitis is classified anatomically as anterior, intermediate, posterior, or diffuse. Anterior uveitis affects the anterior portion of the eye, including the iris. Intermediate uveitis, also called peripheral uveitis, is centered in the area immediately behind the iris and lens in the region of the ciliary body. Posterior uveitis may also constitute a form of retinitis, or it may affect the choroids or the optic nerve. Diffuse uveitis involves all parts of the eye.

Glaucoma is made up of a collection of eye diseases that cause vision loss by damage to the optic nerve. Elevated intraocular pressure (IOP) due to inadequate ocular drainage is a primary cause of glaucoma. Glaucoma can develop as the eye ages, or it can occur as the result of an eye injury, inflammation, tumor or in advanced cases of cataract or diabetes. It can also be caused by certain drugs such as steroids. Further, glaucoma can develop in the absence of elevated IOP. This form of glaucoma has been associated with inheritance (i.e., family history of normal-tension glaucoma) Japanese ancestry, as well as systemic heart disease, such as irregular heartbeat.

The eye produces about one teaspoon of aqueous humor daily. Normally, this fluid escapes from the eye through a spongy mesh of connective tissue called the trabecular meshwork at the same rate at which it is produced. Free radicals and other reactive oxygen species (ROS) cause gradual damage to the trabecular meshwork over a period of time. As a result, the trabecular meshwork becomes partially blocked, outflow facility decreases and the IOP builds up as more aqueous humor is formed. Though the IOP does not rise high enough to cause any noticeable symptoms initially, when pressure remains elevated or continues to rise, fibers in the optic nerve are compressed and destroyed, leading to a gradual loss of vision over a period of years. Izzotti et al. provide convincing evidence linking oxidative DNA damage in a small but critical tissue structure in the outflow system to glaucoma (Izzotti A, Sacca S C, Cartiglia C, De Flora S. Oxidative deoxyribonucleic damage in the eyes of glaucoma patients. Am J. Med. 2003; 114:638-646). They observed a more than threefold increase in the amount of 8-oxo-deoxyguanosine (8-OH-dG) in the trabecular meshwork tissue of glaucoma patients. The increased oxidative DNA damage correlated further with clinical parameters, such as intraocular pressure indexes and visual field loss.

The primary features of the optic neuropathy in glaucoma include characteristic changes in the optic nerve head, a decrease in number of surviving retinal ganglion cells, and loss of vision. It has been proposed that a cascade of events links degeneration of the optic nerve head with the slow death of retinal ganglion cells observed in the disease, and that this cascade of events can be slowed or prevented through the use of neuroprotective agents (Osborne et al., 2003, Eur. J. Ophthalmol. 13 ( Supp 3): S19-S26), of which antioxidants and free radical scavengers are an important class (Hartwick, 2001, Optometry and Vision Science 78: 85-94).

The eye's outermost layer, the cornea, controls and focuses the entry of light into the eye. The cornea must remain transparent to refract light properly. The cornea also helps to shield the rest of the eye from germs, dust, and other harmful matter, and, significantly, it serves as a filter to screen out some of the most damaging ultraviolet (UV) wavelengths in sunlight. Without this protection, the lens and the retina would be highly susceptible to injury from UV radiation.

The cornea and surrounding conjunctiva are also subject to a variety of deleterious conditions that can impair vision. These include inflammatory responses, such as those resulting from allergic reaction, infection or trauma, and a variety of dystrophies (conditions in which one or more parts of the cornea lose their normal clarity due to a buildup of cloudy material), such as Fuchs' dystrophy, keratoconus, lattice dystrophy, and map-dot-fingerprint dystrophy, to name a few, as well as other disorders (e.g., dry eye syndrome).

Ocular surface and lacrimal gland inflammation has been identified in dry eye that plays a role in the pathogenesis of ocular surface epithelial disease, termed keratoconjunctivitis sicca. Both oxidative tissue damage and polymorphonuclear leukocytes indicating an oxidative potential occur in the tear film of patients suffering from dry eyes. These reactions lead to severe damage of the involved tissue. Free radicals and inflammation may be involved in the pathogenesis or in the self-propagation of the disease. (Augustin, A. J. et al., "Oxidative reactions in the tear fluid of patients suffering from dry eyes" Graefe's Arch. Clin.l Exp.l Ophthalmol. 1995, 11:694-698).

Blepharitis is an inflammation of the eyelids. Blepharoconjunctivitis is an inflammation of the eyelids and the conjunctiva of the eye. Both conditions are associated with the condition known as ocular rosacea, though other causes can be present. Blepharitis is an abnormal condition wherein the tears produced contain an excess of lipids (the oily ingredient in natural tears) and, in some cases, contain an irritating oil as well. As explained hereinafter, this oil ingredient serves to prevent evaporation of the aqueous layer that wets the corneal epithelium of the eye and helps spread the aqueous layer over the normally aqueous-resistant cornea during a blink. If excess oil is present, the lipid layer will tend to adhere to the cornea itself. If the eye is unable to clear this oil from the surface of the cornea, a "dry" area occurs on the cornea since the aqueous layer is unable to hydrate this area.

Rosacea is a disease of the skin (acne rosacea) and eyes (ocular rosacea) of unknown etiology and a variety of manifestations. The clinical and pathological features of the eye disease are nonspecific, and the disease is widely underdiagnosed by ophthalmologists.

Retinal phototoxicity is induced by exposure of the eye to retinal illumination from an operating microscope positioned for temporal approach eye surgery or from lasers used by the military. These light sources have the potential for light-induced injury to the fovea (M. A. Pavilack and R. D. Brod "Site of Potential Operating Microscope Light-induced Phototoxicity on the Human Retina during Temporal Approach Eye Surgery" Ophthalmol. 2001, 108(2): 381-385; H. F. McDonald and M. J. Harris "Operating microscope-induced retinal phototoxicity during pars plana vitrectomy" Arch. Ophthalmol. 1988 106:521-523; Harris M. D. et al. "Laser eye injuries in military occupations" Aviat. Space Environ. Med. 2003, 74(9): 947-952). Damage may also occur upon treatment of ablated surface of corneas after excimer laser phototherapy (Seiji Hayashi et al. "Oxygen free radical damage in the cornea after excimer laser therapy" Br. J. Ophthalmol. 1997, 81:141-144).

Certain corneal disorders are not correctable and may be remedied only by corneal transplant, while others may be corrected by phototherapeutic keratectomy (PTK), i.e., eximer laser surgery, the process of which is also known to cause an inflammatory response, causing corneal hazing or areas of corneal opacification.

The skin around the eyes is also subject to disease and disorders. In particular, rosacea of the eyelids and blepharitis are disorders which can be severe. Ocular rosacea is a common and potentially blinding eye disorder with an uncertain etiology (Stone D. U. and J. Chodosh, 2004 Curr. Opin. Ophthalmol. 15(6):499-502). Blepharitis of the eyes may be Staphylococcal blepharitis, seborrheic blepharitis, mixed forms of these, or the most severe form, ulcerative blepharitis.

Oxidative stress has been implicated in the development or acceleration of numerous ocular diseases or disorders, including AMD and the various retinopathies described above (see, e.g., Ambati et al., 2003, Survey of Ophthalmology 48: 257-293; Berra et al., 2002, Arch. Gerontol. Geriatrics 34: 371-377), as well as uveitis (e.g., Zamir et al., 1999, Free Rad. Biol. Med. 27: 7-15), cataract (e.g., M. Lou, 2003, Prog. Retinal & Eye Res. 22: 657-682), glaucoma (e.g., Babizhayev & Bunin, 2002, Curr. Op. Ophthalmol. 13: 61-67), corneal and conjuctival inflammations, various corneal dystrophies, post-surgical or UV-associated corneal damage (e.g., Cejkova et al., 2001, Histol. Histopathol. 16: 523-533; Kasetsuwan et al., 1999, Arch. Ophthalmol. 117: 649-652), and presbyopia (Moffat et al., 1999, Exp. Eye Res. 69: 663-669). For this reason, agents with anti-oxidative properties have been investigated as potential therapeutic agents for the treatment of such disorders. Many investigations have focused on the biochemical pathways that generate reducing power in cells, for example, glutathione synthesis and cycling. Enzymes, such as superoxide dismutase, that reduce activated oxygen species have also been studied to determine whether they diminish cellular oxidative stress. Compounds for inhibiting lipid oxidation in cell membranes by direct radical scavenging have also been considered to be promising therapeutic interventions.

Nitroxides are stable free radicals that are reducible to their corresponding hydroxylamines. These compounds are of interest because of their radical scavenging properties, mimicking the activity of superoxide dismutase and exerting an anti-inflammatory effect in various animal models of oxidative damage and inflammation. Due to their comparative lack of toxicity, hydroxylamines are preferable to nitroxides as therapeutic agents.

It has been known to provide certain hydroxylamine compositions for the prevention or retardation of cataracts. U.S. Pat. No. 6,001,853, in the name of Zigler, et al., the content of which is incorporated herein by reference, reflects work performed at the National Institutes of Health of the United States. Zigler et al. identified a class of hydroxylamines which, when administered to the eye of a test animal, ameliorated cataract genesis or development. Such administration was necessarily via injection for physico-chemical reasons. While Zigler et al. disclosed that it would be clinically convenient to deliver tempol-H by liquid eye drops, no working example was reported, Zigler's hydroxylamines being actually administered by subconjunctival injections. Zigler's materials were also accompanied by the co-administration of a reducing agent, either via injection, systemically or otherwise. It is believed that subsequent work at the National Institutes of Health was directed to the identification of effective hydroxylamines that could be administered topically, however those efforts were not successful.

Accordingly, it has been the object of intense research activity to identify compounds and compositions containing them that can ameliorate cataract formation and development in the eyes of patients, without the need for unpleasant, inconvenient and potentially dangerous intraocular injections. In particular, a long-felt need has existed, which has not been fulfilled, for such compounds and compositions which can be administered via topical application, especially via eye drops.

SUMMARY OF THE INVENTION

The present invention provides compositions for the treatment of cataracts in the eyes of patients either who are developing cataracts or who are known or suspected of being at risk for formation of cataracts. Compositions are also provided for the treatment of macular degeneration, various retinopathies, glaucoma, uveitis, certain disorders of the cornea, eye lid or conjuctiva, and presbyopia in the eyes of patients who exhibit or are at risk of developing such diseases or degenerative conditions. In accordance with preferred embodiments, such compositions are formulated in topical liquid form, especially as eye drops. Periodic application of the compositions of this invention retards or halts development of cataracts or macular degeneration in treated eyes. The invention provides compositions, which need not be applied via injection or other uncomfortable or inconvenient routes.

In accordance with preferred embodiments, the present invention provides compositions comprising an ophthalmologically acceptable carrier or diluent and a compound having the formula:

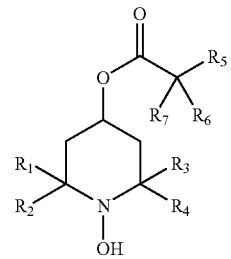

In such compounds, $R_1$ and $R_2$ are, independently, H or $C_1$ to $C_3$ alkyl and $R_3$ and $R_4$ are, independently $C_1$ to $C_3$ alkyl. It is also possible, in accordance with certain embodiments, that $R_1$ and $R_2$, taken together, or $R_3$ and $R_4$, taken together, or both form a cycloalkyl moiety. In the compounds of the invention, $R_5$ is H, OH, or $C_1$ to $C_6$ alkyl while $R_6$ is $C_1$ to $C_6$ alkyl, alkenyl, alkynyl, or substituted alkyl or alkenyl. $R_7$ is $C_1$ to $C_6$ alkyl, alkenyl, alkynyl, or substituted alkyl or alkenyl or $C_1$-$C_6$ cycloalkyl or heterocyclic. It is also possible for $R_6$ and $R_7$, or $R_5$, $R_6$ and $R_7$, taken together, to form a carbocycle or heterocycle having from 3 to 7 atoms in the ring. The term "ophthalmic," as used herein, means to have usefulness in the treatment of the eye and its diseases.

In the compounds used in the compositions of the invention, the substituted alkyl or alkenyl species can be substituted with at least one hydroxy, alkoxy, alkylthio, alkylamino, dialkylamino, aryloxy, arylamino, benzyloxy, benzylamino or heterocyclic or YCO-Z where Y is O, N, or S and Z is alkyl, cycloalkyl or heterocyclic or aryl substituent. In accordance with some embodiments, the heterocycle is a 5, 6, or 7 membered ring with at least one oxygen, sulfur, or nitrogen atom in the ring. In one preferred composition, $R_6$ and $R_7$, taken together are cyclopropyl, while in others, $R_6$ and $R_7$, taken together are tetrahydrofuranyl and $R_5$, $R_6$ and $R_7$ taken together are furanyl.

For certain preferred compounds, each of $R_1$ through $R_4$ is $C_1$ to $C_3$ alkyl, most especially ethyl or methyl, most especially, methyl. For some preferred embodiments, the compounds of the invention $R_6$ is $C_1$ to $C_6$ alkyl substituted with at least one $C_1$ to $C_6$ alkoxy or benzyloxy group.

In other preferred compounds, each of $R_1$ through 4 is methyl, $R_5$ is H or methyl, $R_6$ is methyl substituted with benzyloxy or $C_1$ to $C_6$ alkoxy and $R_7$ is methyl or where $R_6$ and $R_7$ form a cyclopropyl group. In others, each of $R_1$ through $R_4$ is methyl, $R_5$ is methyl, $R_6$ is ethoxy methyl and $R_7$ is methyl. In still others, each of $R_1$ through $R_4$ is methyl, $R_5$ is methyl, $R_6$ is benzyloxy methyl and $R_7$ is methyl, while compounds where each of $R_1$ through $R_4$ is methyl, $R_5$ is methyl, $R_6$ is hydroxymethyl and $R_7$ is methyl also find utility.

Also preferred for some embodiments, are compounds wherein each of $R_1$ through $R_4$ is methyl and $R_5$, $R_6$, and $R_7$ form a furanyl group or where $R_5$ is H and $R_6$ and $R_7$ form a tetrahydrofuranyl group. A further embodiment provides compounds where $R_1$ through $R_4$ are all methyl, $R_5$ is H, and $R_6$ and $R_7$ form a cyclopropyl ring.

It is preferred that the compositions of the invention be formulated into an aqueous medium, which may be delivered in topical liquid form to the eye, via eye drops for example. Accordingly, pH and other characteristics of compositions of the invention are ophthalmologically acceptable for topical application to the eye of a patient. For some embodiments, the compound is in the form of a salt, preferably a hydrochloride or similar salt.

The compositions of the invention may contain more than one compound of the invention. Furthermore, the compositions may contain another compound known in the art for use in the treatment of a particular indication in combination with the compound(s) of the invention. In some embodiments, the compounds of the invention are administered simultaneously. In other embodiments, the compounds of the invention are administered sequentially. Likewise, other compounds known in the art for use in the treatment of the diseases and disorders described herein may be administered with the compound(s) of the invention either simultaneously or sequentially. The invention also provides methods of treatment of diseases and disorders using such combination therapy.

Since the compounds of the invention contain oxidizable hydroxylamine moieties, which are most effective in the chemically reduced state, in certain embodiments the compositions preferably further comprise an anti-oxidant agent, especially a sulfhydryl compound. Exemplary compounds include mercaptopropionyl glycine, N-acetylcysteine, β-mercaptoethylamine, glutathione and similar species, although other anti-oxidant agents suitable for ocular administration, e.g. ascorbic acid and its salts or sulfite or sodium metabisulfite may also be employed. The amount of hydroxylamines may range from about 0.1% weight by volume to about 10.0%; weight by volume and preferred is about 0.25%-weight by volume to about 10.0% weight by volume.

The invention can also be seen to provide ophthalmologic compositions comprising an ophthalmologically acceptable carrier or diluent together with a compound having an N-hydroxypiperidine portion bound to a solubility modifying portion. In this way, the active moiety, hydroxylamine, can be delivered to the lens of an eye in need of treatment in a "stealth" form, that is, in the form of a chemical compound that can have the hydroxylamine portion cleaved from the balance of the molecule. The compound is broken down in the eye to give rise to the active hydroxylamine species for effective treatment of cataracts, macular degeneration or any of the other eye disorders referred to herein. The compound thus provided has a solubility in water at 25° C. of at least about 0.1% by weight and a water—n-octanol partition coefficient at 25° C. of at least about 3. In accordance with preferred embodiments, the water solubility is greater than about 0.5% by weight, preferably greater than about 2.0% and the partition coefficient is greater than about 5, preferably greater than about 10.

Accordingly, it is desired that the compounds used be such that, upon administration topically to the eye, they penetrate the cornea and are converted to the desired hydroxylamine, preferably, an N-hydroxypiperidine. It is preferred that this conversion occurs through enzymatic cleavage of the compound. In one preferred embodiment, the hydroxylamine portion comprises—1,4-dihydroxy-2,2,6,6-tetramethylpiperidine.

The invention includes methods for ameliorating—either slowing or arresting entirely—the development of a cataract in the lens of a patient. Likewise, the invention includes methods for ameliorating the development of, or otherwise treating, presbyopia, macular degeneration, various retinopathies, glaucoma, uveitis, corneal disorders (particularly those associated with trauma, inflammation (both of which can be caused by eximer laser surgery), aging, UV exposure and other oxidative-related disorders), disorders of the conjunctiva (conjunctivitis), dry eye syndrome, blepharitis and rosacea of the eye. The invention also provides methods for protecting retinal pigment epithelium against photooxidative damage. In one embodiment, the methods comprise administering to the eye an ophthalmologic composition comprising an ophthalmologically acceptable carrier or diluent in the form of eye drops containing a compound having one or more of the foregoing compounds as an active ingredient therein. It is preferred that the administration takes place a plurality of time and, in certain preferred embodiments, chronic, periodic administration is performed.

In another aspect of the invention, ophthalmic compositions of the invention are used as a prophylactic treatment to prevent or delay development of certain age-related ocular conditions, including cataracts, presbyopia, corneal degeneration and dystrophy, glaucoma, macular degeneration and photooxidative retinal damage. In preferred embodiments the compositions are formulated as eyedrops or eye washes. They are administered to the eye prior to, or at the initial stages of, development of age-related conditions of the eye, or to prevent progression of later stage disease.

The invention also provides methods for identifying pharmaceuticals that can be delivered to the lens of a patient in the form of eye drops. These methods comprise selecting a compound having a water solubility at 25° C. of at least about 0.1% by weight and a water/n-octanol partition coefficient of at least about 5 at 25° C., which compound is enzymatically cleavable under conditions obtaining in the eye of a patient to give rise to a proximate drug for treatment of a condition of the eye, preferably the lens. Preferably, the active pharmaceutical species is a hydroxylamine, especially one having an N-hydroxypiperidine nucleus.

DETAILED DESCRIPTION OF ILLUSTRATIVE EMBODIMENTS

Figure 1:
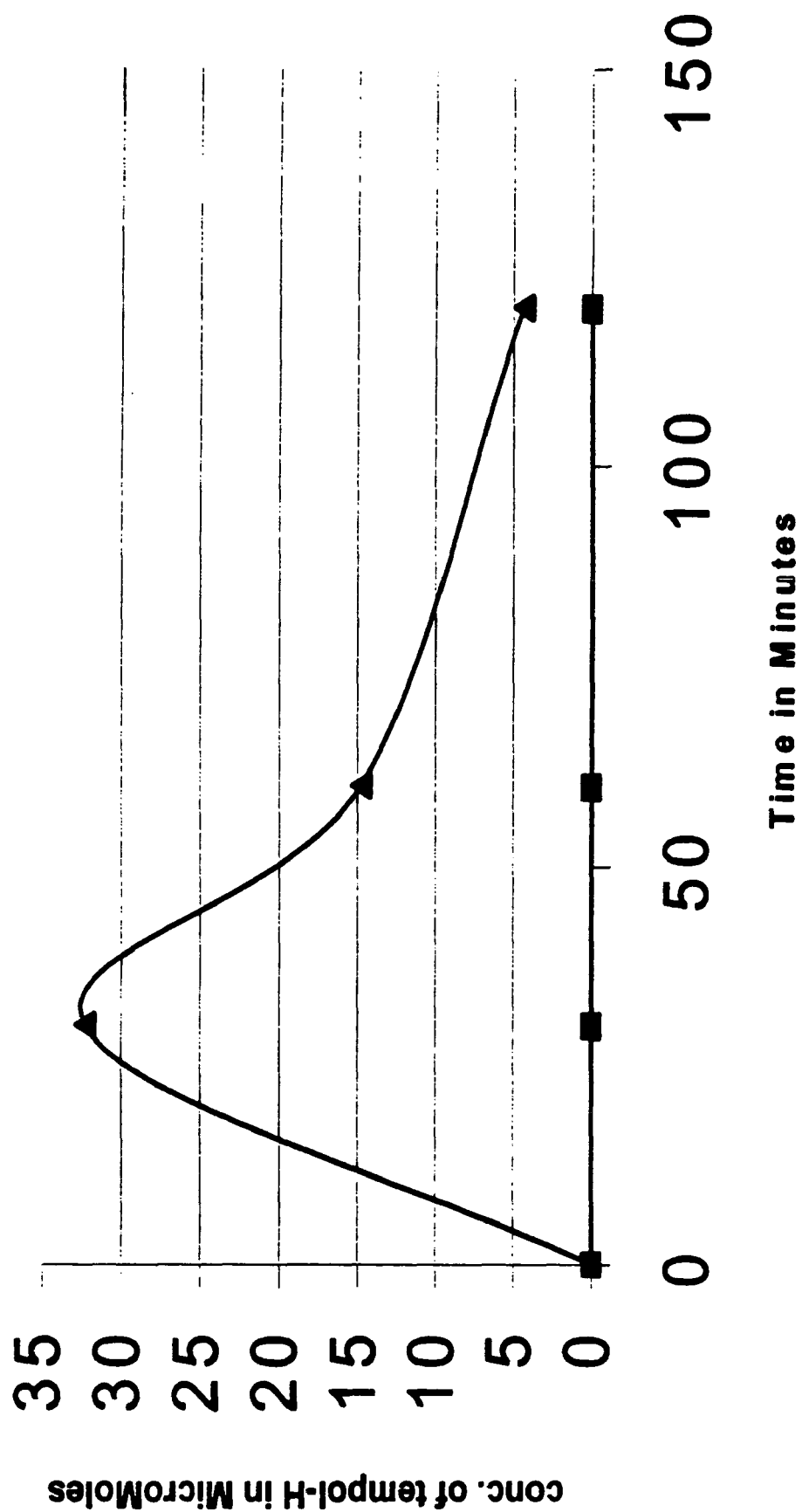
FIG. 1 depicts aqueous humor levels of tempol-H (1,4-dihydroxy-2,2,6,6-tetramethylpiperidine) in rabbit eyes treated topically with Compound 1 of the invention or with tempol-H.

The present invention provides compounds and compositions that can be administered topically to the eyes of patients who exhibit, or who are developing or are at risk of developing cataracts, presbyopia, uveitis, macular degeneration or other retinopathies, including but not limited to diabetic retinopathy, choroidal neovascular membrane (CNVM), cystoid macular edema (CME), epi-retinal membrane (ERM) (macular pucker) and macular hole, as well as disorders of the cornea (and surrounding eye lids and conjuctiva), including but not limited to inflammation, trauma, irradiation damage, corneal neovascularization and various dystrophies such as Fuch's dystrophy, keratoconus, lattice dystrophy and map-dot-fingerprint dystrophy, as well as dry eye syndrome, blepharitis and rosacea of the eye. While such compounds may be seen to include as a chemical fragment, hydroxylamine species previously known to be effective in retarding cataract development, the achievement of compounds that can be topically applied is a very significant advance in the therapeutic arts. Indeed, the National Institutes of Health, assignee of the Zigler patent; tried, but failed to identify compounds that could be efficacious in therapies for cataracts or macular degeneration through topical application. In this context, it is noted that the Zigler patent recites administration of certain compositions such as tempol-H via injection and recognizes the desirability of topical administration via eye drops, however, this proposed route of administration was not found to be available in practice. Accordingly, the present invention should be viewed as "pioneering" and as having satisfied a long-felt, but unserved need in the art.

The inventors have demonstrated that the compounds of the present invention are absorbed into and across the cornea and sclera, through the uvea and into the lens and interior of the eye. Enzymatic processes within these tissues cleave the N-hydroxypiperidine portion of the compound from the acid to which it was esterified. The N-hydroxypiperidine moiety, once liberated, then performs the same functions with the same efficacy as demonstrated by Zigler. Additionally, a further advantage of the compounds of the invention is that, even in their esterified form, they have been found to possess free radical-scavenging and antioxidant activities as seen in tempol-H and other non-esterified hydroxylamine compounds.

The compounds of the invention have not been known heretofore for administration to the eye. They have certainly not been known for use in the treatment of cataract, presbyopia, corneal disorders, macular degeneration, retinopathies, glaucoma or uveitis. U.S. Pat. No. 5,981,548, in the name of Paolini, et al., the content of which is incorporated herein by reference, depicts certain N-hydroxylpiperidine esters and their use as antioxidants in a number of contexts. However, Paolini does not disclose ophthalmologic formulations or topical treatment of the eyes of patients. Paolini does disclose, however, useful syntheses for certain molecules of this type.

Gupta et al. in U.S. Pat. No. 4,404,302, the content of which, disclose the use of certain N-hydroxylamines as light stabilizers in plastics formulations. Mitchell et al. in U.S. Pat. No. 5,462,946, the content of which is incorporated herein by reference, discloses certain nitroxides deriving from substituted oxazolidines for protection of organisms from oxidative stress. U.S. Pat. No. 3,936,456, the content of which is incorporated herein by reference, in the name of Ramey et al., provides substituted piperazine dione oxyls and hydroxides for the stabilization of polymers. U.S. Pat. No. 4,691,015, to Behrens et al., the content of which is incorporated herein by reference, describes hydroxylamines derived from hindered amines and the use of certain of them for the stabilization of polyolefins.

In one aspect, the present invention provides compositions comprising a pharmaceutically carrier or diluent and a compound having the formula:

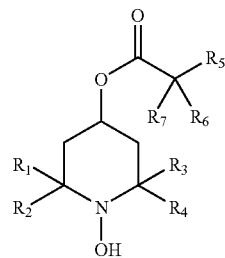

where $R_1$ and $R_2$ are, independently, H or $C_1$ to $C_3$ alkyl;
$R_3$ and $R_4$ are, independently $C_1$ to $C_3$ alkyl; and
where $R_1$ and $R_2$, taken together, or $R_3$ and $R_4$, taken together, or both may be cycloalkyl;
$R_5$ is H, OH, or $C_1$ to $C_6$ alkyl;
$R_6$ is $C_1$ to $C_6$ alkyl, alkenyl, alkynyl, or substituted alkyl or alkenyl;
$R_7$ is $C_1$ to $C_6$ alkyl, alkenyl, alkynyl, substituted alkyl, alkenyl, cycloalkyl, or heterocycle
or where $R_6$ and $R_7$, or $R_5$, $R_6$ and $R_7$, taken together, form a carbocycle or heterocycle having from 3 to 7 atoms in the ring. These compounds may also be used with ophthalmically acceptable carriers for use in ophthalmic compositions.

In another aspect, the present invention provides an ophthalmically acceptable carrier or diluent and a compound having an N-hydroxy piperidine portion bound to a solubility modifying portion, the compound having a solubility in water at 25° C. of at least about 0.25% by weight and a water—n-octonal partition coefficient at 25° C. of at least about 5. The composition may have the N-hydroxy piperidine portion cleavable from the compound under conditions found in the eye. It is foreseeable that this portion is cleaved under conditions in the lens of the eye. The N-hydroxy piperidine portion may be cleaved enzymatically. The compositions may also exist wherein the N-hydroxy piperidine portion is 1-oxyl-4-hydroxy-2,2,6,6-tetramethylpiperidyl.

The term $C_1$ to $C_n$ alkyl, alkenyl, or alkynyl, in the sense of this invention, means a hydrocarbyl group having from 1 to n carbon atoms in it. The term thus comprehends methyl, ethyl, n-propyl, iso-propyl, n-butyl, sec-butyl, iso-butyl, tert-butyl, and the various isomeric forms of pentyl, hexyl, and the like. Likewise, the term includes ethenyl, ethynyl, propenyl, propynyl, and similar branched and unbranched unsaturated hydrocarbon groups of up to n carbon atoms. As the context may admit, such groups may be functionalized such as with one or more hydroxy, alkoxy, alkylthio, alkylamino, dialkylamino, aryloxy, arylamino, benzyloxy, benzylamino, heterocycle, or YCO-Z, where Y is O, N, or S and Z is alkyl, cycloalkyl, heterocycle, or aryl substituent.

The term carbocycle defines cyclic structures or rings, wherein all atoms forming the ring are carbon. Exemplary of these are cyclopropyl, cyclobutyl, cyclopentyl, cyclohexyl, cycloheptyl, etc. Cyclopropyl is one preferred species. Heterocycle defines a cyclic structure where at least one atom of the ring is not carbon. Examples of this broad class include furan, dihydrofuran, tetrahydrofuran, pyran, oxazole, oxazoline, oxazolidine, imidazole and others, especially those with an oxygen atom in the ring. Five, six and seven membered rings with at least one oxygen or nitrogen atom in the ring are preferred heterocycles. Furanyl and tetrahydrofuranyl species are among those preferred.

It is preferred for certain embodiments that each of $R_1$ through $R_4$ be lower alkyl that is $C_1$ to $C_3$ alkyl. Preferably, all these groups are methyl for convenience in synthesis and due to the known efficacy of moieties having such substitution at these positions. However, other substituents may be used as well.

In certain embodiments, compounds are employed where $R_6$ is $C_1$ to $C_6$ alkyl substituted with at least one $C_1$ to $C_6$ alkoxy or benzyloxy group. Preferred among these are compounds having ethoxy or benzyloxy substituents. Among preferred compounds are those where each of $R_1$ through $R_4$ is methyl, $R_5$ is H or methyl, $R_6$ is methyl substituted with benzyloxy or $C_1$ to $C_6$ alkoxy, and $R_7$ is methyl or where $R_6$ and $R_7$ form a cyclopropyl group as well as the compound in which each of $R_1$ through $R_4$ is methyl, $R_5$ is methyl, $R_6$ is ethoxy or benzyloxy methyl, and $R_7$ is methyl. An additional preferred compound is one in which each of $R_1$ through $R_4$ is methyl, $R_5$ is methyl, $R_6$ is hydroxymethyl, and $R_7$ is methyl.

Other useful compounds are those wherein each of $R_1$ through $R_4$ is methyl, and $R_5$, $R_6$, and $R_7$ form a furanyl group, or in which $R_6$ and $R_7$ form a tetrahydrofuranyl group. The compound where $R_1$ through $R_4$ is methyl, $R_5$ is H and, $R_6$ and $R_7$ form a cyclopropyl ring is a further preferred species are as those set forth in the examples below.

The compounds of the invention are formulated into compositions for application to the eye of patients in need of therapy. Thus, such compositions are adapted for pharmaceutical use as an eye drop or in contact lenses, inserts or the like, as described in greater detail below. Accordingly, formulation of compound into sterile water containing any desired diluents, salts, pH modifying materials and the like as are known to persons skilled in the pharmaceutical formulations art may be performed in order to achieve a solution compatible with administration to the eye. It may be that eye drops, inserts, contact lenses, gels and other topical liquid forms may require somewhat different formulations. All such formulations consistent with direct administration to the eye are comprehended hereby.

The compositions of the invention may also have antioxidants in ranges that vary depending on the kind of antioxidant used. The usage also depends on the amount of antioxidant needed to allow at least 2 years shelf-life for the pharmaceutical composition. One or more antioxidants may be included in the formulation. Certain commonly used antioxidants have maximum levels allowed by regulatory authorities. As such, the amount of antioxidant(s) to be administered should be enough to be effective while not causing any untoward effect. Such doses may be adjusted by a physician as needed, within the maximum levels set by regulatory authorities, and is well within the purview of the skilled artisan to determine the proper and effective dose. Reasonable ranges are about 0.01% to about 0.15% weight by volume of EDTA, about 0.01% to about 2.0% weight volume of sodium sulfite, and about 0.01% to about 2.0% weight by volume of sodium metabisulfite. One skilled in the art may use a concentration of about 0.1% weight by volume for each of the above. N-Acetylcysteine may be present in a range of about 0.1% to about 5.0% weight by volume, with about 0.1% to about 10% of hydroxylamine concentration being preferred. Ascorbic acid or salt may also be present in a range of about 0.1% to about 5.0% weight by volume with about 0.1% to about 10% weight by volume of hydroxylamine concentration preferred. Other sulfhydryls, if included, may be the same range as for N-acetylcysteine. Other exemplary compounds include mercaptopropionyl glycine, N-acetyl cysteine, β-mercaptoethylamine, glutathione and similar species, although other antioxidant agents suitable for ocular administration, e.g. ascorbic acid and its salts or sulfite or sodium metabisulfite may also be employed.

A buffering agent may be used to maintain the pH of eye drop formulations in the range of about 4.0 to about 8.0; this is necessary to prevent corneal irritation. Because the compounds of this invention are esters, the pH is preferably maintained at about 3.5 to about 6.0, preferably about 4.0 to about 5.5, in order to prevent hydrolysis of the ester bond and to ensure at least a 2-year shelf life, for the product. This pH also ensures that most of the hydroxylamine is in its protonated form for highest aqueous solubility. The buffer may be any weak acid and its conjugate base with a pKa of about 4.0 to about 5.5; e.g. acetic acid/sodium acetate; citric acid/sodium citrate. The pKa of the hydroxylamines is about 6.0. For direct intravitreal or intraocular injection, formulations should be at pH 7.2 to 7.5, preferably at pH 7.3-7.4.

The compounds of the present invention may also include tonicity agents suitable for administration to the eye. Among those suitable is sodium chloride to make formulations of the present invention approximately isotonic with 0.9% saline solution.

In certain embodiments, the compounds of the invention are formulated with viscosity enhancing agents. Exemplary agents are hydroxyethylcellulose, hydroxypropylcellulose, methylcellulose, and polyvinylpyrrolidone. The viscosity agents may exists in the compounds up to about 2.0% weight by volume. It may be preferred that the agents are present in a range from about 0.2% to about 0.5% weight by volume. A preferred range for polyvinylpyrrolidone may be from about 0.1% to about 2.0% weight by volume. One skilled in the art may prefer any range established as acceptable by the Food and Drug Administration.

The compounds of the invention may have co-solvents added if needed. Suitable cosolvents may include glycerin, polyethylene glycol (PEG), polysorbate, propylene glycol, mannitol and polyvinyl alcohol. The presence of the co-solvents may exist in a range of about 0.2% to about 4.0% weight by volume. It may be preferred that mannitol may be formulated in the compounds of the invention in a range of about 0.5% to about 4.0% weight by volume. It may also be preferred that polyvinyl alcohol may be formulated in the compounds of the invention in a range of about 0.1% to about 4.0% weight by volume. One skilled in the art may prefer ranges established as acceptable by the Food and Drug Administration.

Preservatives may be used in the invention within particular ranges. Among those preferred are up to 0.013% weight by volume of benzalkonium chloride, up to 0.013% weight by volume of benzethonium chloride, up to 0.5% weight by volume of chlorobutanol, up to 0.004% weight by volume or phenylmercuric acetate or nitrate, up to 0.01% weight by volume of thimerosal, and from about 0.01% to about 0.2% weight by volume of methyl or propylparabens.

Formulations for injection are preferably designed for single-use administration and do not contain preservatives. Injectable solutions should have isotonicity equivalent to 0.9% sodium chloride solution (osmolality of 290-300 mOsmoles). This may be attained by addition of sodium chloride or other co-solvents as listed above, or excipients such as buffering agents and antioxidants, as listed above. Injectable formulations are sterilized and, in one embodiment, supplied in single-use vials or ampules. In another embodiment, injectable products may be supplied as sterile, freeze-dried solids for reconstitution and subsequent injection.

The compositions of the invention may contain more than one compound of the invention. Thus the compositions of the invention contain at least one compound of the invention. In some embodiments, the compounds of the invention are administered simultaneously. In other embodiments, the compounds of the invention are administered sequentially. The methods of the invention include combination therapy.

In some embodiments of the invention, the compound(s) of the invention are administered with another compound known in the art that is useful for treating a disease or disorder that is the target of the compounds of the invention. Thus the composition of the invention may further contain at least one other compound known in the art for treating the disease or disorder to be treated. The other compound(s) known in the art may be administered simultaneously with the compound(s) of the invention, or may be administered sequentially. Similarly, the methods of the invention include using such combination therapy.

The tissues, including the lens, of the anterior chamber of the eye are bathed by the aqueous humor. This fluid is in a highly reducing redox state because it contains antioxidant compounds and enzymes. The lens is also a highly reducing environment, which maintains the hydroxlamine compounds in the preferred reduced form. Therefore, it may be advantageous to include a reducing agent in the eye drop formulation, or to dose separately with a reducing agent to maintain the hydroxylamine in its reduced form.

Preferred reducing agents may be N-acetylcysteine, ascorbic acid or a salt form, and sodium sulfite or metabisulfite, with ascorbic acid and/or N-acetylcysteine or glutathione being particularly suitable for injectable solutions. A combination of N-acetylcysteine and sodium ascorbate may be used in various formulations. A metal chelator antioxidant, such as EDTA (ethylenediaminetetraacetic acid) or possibly DTPA (diethylenetriaminepentaacetic acid) may also be added to keep the hydroxylamine in the reduced form in the eye drop formulation.

It is noteworthy that the compounds of the invention exert their anti-caractogenic and other therapeutic effects in two ways. First, the ester compounds are hydrolyzed in situ to form hydroxylamine components that exert therapeutic activity. Second, the esterified compounds themselves possess anti-caractogenic and antioxidant activity, thereby supporting the therapeutic efficacy of pharmaceutical preparations comprising the compounds.

In connection with the first basis for activity of the compounds of the invention, i.e., cleavage to liberate hydroxylamine components, numerous esterases are known to be present in ocular tissues, especially the cornea. The specific esterase(s) that cleaves the esters of the present series need not be identified in order to practice the invention. The cleavage of the esters occurs rapidly and essentially completely on administering the compounds to the eyes of rabbits. This is shown by the presence of tempol-H in the aqueous humor at all times (30, 60, 90 and 120 minutes) examined after topical dosing. In contrast, the esters are stable in aqueous solutions; e.g. solution of Ester 4 at 40° C., in acetate buffer at pH 4.6, is stable for 3 months.

The present invention has optimal use in ameliorating the development of a cataract in the eye of a patient. Another optimal use includes the treatment of macular degeneration in the retina of a patient. Yet other optimal uses include treatment, reduction or prevention of the development of diabetic retinopathy and various other retinopathies as described herein, as well as the treatment of uveitis and glaucoma. Still another optimal use is the treatment of corneal disorders, particularly those associated with oxidative stress, such as inflammation or trauma (which can be, but are not necessarily, associated with surgery) and various dystrophies. The compounds and compositions of the invention may also be used to reduce, prevent or ameliorate photooxidative damage to retinal pigment epithelium, and for amelioration of irritation and inflammation during laser surgery of the eye, including trabeculectomy treatment for glaucoma and keratectomy for corneal reshaping. The compounds and compositions may also be used to treat diseases and disorders of the conjunctiva and eyelids. Further, the compounds and compositions of the invention may be used to treat alopecia and damage to rectal tissue following radiation therapy.

Many of the disorders and conditions described herein, particularly cataract, presbyopia and macular degeneration, are progressive conditions of the aging process. Accordingly, the compositions of the invention may be used to advantage as a prophylactic treatment to prevent or delay development of these age-related ocular conditions. In preferred embodiments the compositions are formulated as eyedrops or eye washes. They are administered to the eye prior to, or at the initial stages of, development of age-related conditions of the eye.

Compositions comprising the compounds of the invention may be delivered to the eye of a patient in one or more of several delivery modes known in the art. In a preferred embodiment, the compositions are topically delivered to the eye in eye drops or washes. In another embodiment, the compositions are delivered in a topical ophthalmic ointment, which is particularly useful for treating conditions of the cornea, conjuctiva or surrounding skin, such as dry-eye and blepharitis. In another embodiment, the compositions may be delivered to various locations within the eye via periodic subconjunctival or intraocular injection, or by infusion in an irrigating solution such as BSS® or BSS PLUS® (Alcon USA, Fort Worth, Tex.) or by using pre-formulated solutions of the hydroxylamines in compositions such as BSS® or BSS PLUS®. In one embodiment, the use of the compounds of the invention in vitrectomy may be effective in reducing or preventing the development of vitrectomy-associated cataracts.

Alternatively, the compositions may be applied in other ophthalmologic dosage forms known to those skilled in the art, such as pre-formed or in situ-formed gels or liposomes, for example as disclosed in U.S. Pat. No. 5,718,922 to Herrero-Vanrell. A direct injection of drugs into the vitreous body used for treating diseases has been used, in which microspheres or liposomes were used to release drugs slowly (Moritera, T. et al. "Microspheres of biodegradable polymers as a drug-delivery system in the vitreous" *Invest. Ophthalmol. Vis. Sci.* 1991 32(6): 1785-90).

In another embodiment, the composition may be delivered to or through the lens of an eye in need of treatment via a contact lens (e.g. Lidofilcon B, Bausch & Lomb CW79 or DELTACON (Deltafilcon A) or other object temporarily resident upon the surface of the eye. For example, U.S. Pat. No. 6,410,045 describes a contact lens-type drug delivery device comprising a polymeric hydrogel contact lens containing drug substance in a concentration of between 0.05% and 0.25% by weight absorbed in said contact lens which is capable of being delivered into the ocular fluid.

In other embodiments, supports such as a collagen corneal shield (e.g. BIO-COR dissolvable corneal shields, Summit Technology, Watertown, Mass.) can be employed. The compositions can also be administered by infusion into the eyeball, either through a cannula from an osmotic pump (ALZET®, Alza Corp., Palo Alto, Calif.) or by implantation of timed-release capsules (OCCUSENT®) or biodegradable disks (OCULEX®OCUSERT®) which contain the compositions. These routes of administration have the advantage of providing a continuous supply of the composition to the eye.

Many types of drug delivery systems are known in the art and can be used for delivery of compositions of the present invention. Non-limiting examples have been set forth above, and more are listed below.

A preferred method to treat dry eye symptoms utilizes aqueous based solutions or gels, which may be formulated to contain one or more compounds of the present invention. The "active" ingredients in these artificial tear formulations are common water soluble or dispersable polymers such as hydroxyethylcellulose, hydroxypropylmethylcellulose, methylcellulose, carboxymethylcellulose, polyvinyl alcohol, polyvinyl pyrrolidone, polyethylene glycol, carbomers and poloxamers.

U.S. Pat. No. 6,429,194 describes aqueous ophthalmic preparations for instillation into the eye, or in which to pre soak or store an object to be inserted into the eye, such as a contact lens, an ointment, or a solid device to be inserted into the conjunctival sac. The ophthalmic preparation includes a mucin component, similar to that found at the normal human ocular surface. U.S. Pat. No. 6,281,192 also describes the ophthalmic applications of mucin.

An ophthalmic solution must provide an effective and long lasting treatment for symptoms of dry eye. One approach to achieving these aims is to provide a solution with tailored rheological properties, that is, a high viscosity solution that yields or flows under stress. Examples of this approach are disclosed in U.S. Pat. Nos. 5,075,104 and 5,209,927, where the rheological properties of the ophthalmic solutions are attained through the use of carbomer polymers. These carbomer polymers have been found to be bio-adhesive as described in U.S. Pat. Nos. 5,225,196; 5,188,828; 4,983,392 and 4,615,697. It is believed that the bio-adhesive properties of the carbomer contributes to longer retention times in the eye. In fact, U.S. Pat. Nos. 5,075,104 and 5,209,927, teach that the carbomer polymers appear to function by maintaining or restoring the normal hydration equilibrium of the epithelial cells, protecting the cornea in a manner similar to that believed to be provided by the mucin component of normal tears.

U.S. Pat. No. 4,883,658 describes a synergistic combination of an aqueous solution of a partially hydrolyzed poly(vinyl acetate) and a fully hydrolyzed poly(vinyl acetate), i.e. poly(vinyl alcohol), exhibiting a low surface tension at the water-air interface, while forming a completely wettable absorbed layer over hydrophobic solids. The combination suitable for use as an aqueous vehicle for topically used ophthalmic drugs or nutrients.

Emulsion based formulations for treating dry eye symptoms have emerged recently. One approach, as disclosed in U.S. Pat. Nos. 5,578,586; 5,371,108; 5,294,607; 5,278,151; 4,914,088, utilize methods and compositions for reducing evaporation of the aqueous layer from the surface of the eye. The method comprises applying an admixture of a charged phospholipid and a non-polar oil over the eye, preferably in the form of a finely divided oil-in-water emulsion. Another approach is described in U.S. Pat. Nos. 4,818,537 and 4,804,539, where liposome compositions in the form of emulsions are reported to enhance retention on ocular surfaces and thereby alleviate the symptoms of dry eye.

Several other types of delivery systems are available that are particularly suitable for delivering pharmaceutical compositions to the interior or posterior of the eye. For instance, U.S. Pat. No. 6,154,671 to Parel et al. discloses a device for transferring a medicament into the eyeball by iontophoresis. The device utilizes a reservoir for holding the active agent, which contains at least one active surface electrode facing the eye tissue lying at the periphery of the cornea. The reservoir also has a return electrode in contact with the patient's partly closed eyelids. U.S. Pat. No. 5,869,079 to Wong et al. discloses combinations of hydrophilic and hydrophobic entities in a biodegradable sustained release ocular implant. In addition, U.S. Pat. No. 6,375,972 to Guo et al., U.S. Pat. No. 5,902,598 to Chen et al., U.S. Pat. No. 6,331,313 to Wong et al., U.S. Pat. No. 5,707,643 to Ogura et al., U.S. Pat. No. 5,466,233 to Weiner et al. and U.S. Pat. No. 6,251,090 to Avery et al. each describes intraocular implant devices and systems that may be used to deliver pharmaceutical compositions comprising compounds of the present invention.

U.S. Pat. No. 4,014,335 describes an ocular drug delivery device placed in the cul-de-sac between the sclera and lower eyelid for administering the drug and acting as a reservoir. The device comprises a three-layered laminate of polymeric materials holding the drug in a central reservoir region of the laminate. The drug diffuses from the reservoir through at least one of the polymeric layers of the laminate.

Solid devices, in the form of ocular inserts, have been utilized for longer term symptomatic relief of dry eye. These devices are placed in the eye and slowly dissolve or erode to provide a thickened tear film. Examples of this technology are given in U.S. Pat. Nos. 5,518,732; 4,343,787, and 4,287,175.

The compounds of this invention can have uses in fields broader than ophthalmology. These areas may include, for example, protection of hair follicles and rectum from radiation damage during radiation therapy for cancer. Other forms of administration of the compositions of the present invention, wherein the delivery to the eye is not called for, may include oral tablets, liquids and sprays; intravenous, subcutaneous and intraperitoneal injections; application to the skin as a patch or ointment; enemas, suppositories, or aerosols.

For effective treatment of cataract, presbyopia, macular degeneration, glaucoma or any of the other retinopathies, corneal disorders or eye conditions described herein, one skilled in the art may recommend a dosage schedule and dosage amount adequate for the subject being treated. The dosing may occur less frequently if the compositions are formulated in sustained delivery vehicles, or are delivered via implant. For topical delivery, it may be preferred that dosing occur one to four times daily for as long as needed. The dosage amount may be one or two drops per dose. The dosage schedule may also vary depending on the active drug concentration, which may depend on the hydroxylamine used and on the needs of the patient. It may be preferred that the active amount be from about 0.1% to about 10.0% weight by volume in the formulation. In some embodiments, it is preferable that the active drug concentration be 0.25% to about 10.0% weight by volume. The concentration of the hydroxylamine component will preferably be in the range of about 0.1 µM to about 10 mM in the tissues and fluids. In some embodiments, the range is from 1 µm to 5 mM, in other embodiments the range is about 10 µM to 2.5 mM. In other embodiments, the range is about 50 µM to 1 mM. Most preferably the range of hydroxylamine concentration will be from 1 to 100 µM. The concentration of the reducing agent will be from 1 µM to 5 mM in the tissues or fluids, preferably in the range of 10 µM to 2 mM. The concentrations of the components of the composition are adjusted appropriately to the route of administration, by typical pharmacokinetic and dilution calculations, to achieve such local concentrations. Alternatively, penetration of cornea and absorption into other tissues in the interior of the eye is demonstrated using radiolabeled hydroxylamine.

An ophthalmologist or one similarly skilled in the art will have a variety of means to monitor the effectiveness of the dosage scheme and adjust dosages accordingly. For example, effectiveness in treating cataract may be determined by the ophthalmologist by observing the degree of opacity of the lens at intervals by slit-lamp examination, or other means known in the art. Effectiveness in the treatment of macular degeneration or other retinopathies may be determined by improvement of visual acuity and evaluation for abnormalities and grading of stereoscopic color fundus photographs. (Age-Related Eye Disease Study Research Group, NEI, NIH, AREDS Report No. 8, 2001, Arch. Ophthalmol. 119: 1417-1436). Effectiveness in the treatment of uveitis may be determined by improvement in visual acuity and vitreous haze and control of inflammation (Foster et al., 2003, Arch. Ophthalmol. 121: 437-40). Following such evaluation, the ophthalmologist may adjust the frequency and/or concentration of the dose, if needed.

Another aspect of the invention features a method of identifying a pharmaceutical for delivery to the eye of a patient in the form of eye drops, which comprises selecting a compound having a water solubility at 25° C. of at least about 0.25% by weight and a water—n-octonal partition coefficient of at least about 5 at 25° C., which compound is enzymatically cleavable under conditions obtained in the lens of the eye of a patient to give rise to a hydroxylamine, preferably an N-hydroxy piperidine. Preferably, the selected compound is an ester of the hydroxylamine.

It may be preferred that at least 0.1% solubility is needed for an eye drop, even for a suspension formulation. Completely water-insoluble compounds may not be effective. Esters that are soluble in water (>0.1% weight by volume) are preferred. Esters with less than 0.1% solubility may be used in the form of suspensions or ointments or other formulations. Solubility is determined by mixing 100 mg of test compound with 1 ml of water, at room temperature and adding additional 1 ml quantities of water, with mixing, until ester dissolves completely.

Corneal penetration is shown by measuring a substantial concentration (e.g. >5 µM) of the effective hydroxylamine and/or ester in the aqueous humor after administering a solution of the compound in vivo to the eyes of rabbits. This is determined by electron spin resonance (ESR), high performance liquid chromatography (HPLC) or gas chromatography (GC) assay of the rabbit aqueous humor. In vitro corneal penetration methods may also be used prior to the in vivo testing method particularly for screening compounds. Penetration of compounds to the interior or posterior of the eye is likewise shown by measuring the concentration of the compound in the vitreous humor, uvea or retina after administering a solution of the compound to the eyes of rabbits.

Esters are selected for these tests based on their calculated or measured octanol/water partition coefficient (P). Hydrophilic compounds such as tempol-H cannot penetrate the lipophilic epithelial layer of the cornea. Partition coefficients of tempol-H and esters that penetrate are as follows:

| | P (Calculated)* |
|---|---|
| Tempol-H | 0.8 (measured, 0.5) |
| Ester 4 | 16.4 |
| Ester 8 | 8.2 |
| Ester 14 | 6.3 |

*Clog P version 4.0, Biobyte Corporation

Enzymatic conversion is essentially complete at greater than 90% hydrolysis of the ester in vivo to the alcohol and acid after administering the compound to the eye of rabbits. The conversion may be determined by HPLC or GC assay of a selected eye tissue (e.g., aqueous humor). Alternatively, the enzymatic conversion may be determined by incubating the compound in plasma or eye tissue homogenate and assaying samples periodically by HPLC or GC to monitor the rate of breakdown. Esters with a half-life of less than about 1 or 2 hours are preferred candidates. This method may be the preferred screening procedure before in vivo testing.

Esters should have less than about 10% hydrolysis at 40° C., after 3 months, in aqueous solution at pH 4.0-5.0. This extrapolates to a shelf life of the ester in solution of at least 18 months at room temperature, which may be preferred for an eye drop product.

EXAMPLES

The present invention is illustrated in certain embodiments by reference to the following examples. The examples are for purposes of illustration only and are not intended to be limiting in any way.

Example 1

Determination of Ester Compound Stability in Aqueous Solution. Method: A 0.1-0.5% solution of the ester compound was prepared in buffer (pH 4.5-5.0) containing DTPA or EDTA. The solution was filled into amber glass vials, which were sealed and placed in a controlled temperature container maintained at 40° C. Sample vials were removed periodically and stored at 0-5° C. until analyzed by HPLC, GC, or GC/MS analytical methods, and found to be stable after 3 months under these conditions.

To be useful as an anti-cataract drug the agent must penetrate into the lens. This may be included in the method for selecting an anti-cataract compound. A description of method for tempol-H follows:

Example 2

Drug Penetration of Organ Cultured Rat Lenses

In contrast to drugs tested previously as anti-cataract agents, tempol-H and tempol have a remarkable ability to penetrate lens tissue from the surrounding fluid. The experiments described in this section determined the time course, active compound concentrations and compound distribution in the lens, after incubation with rat lenses under the organ culture conditions.

Method: Rat lenses were cultured as follows: Rat lenses were obtained from Sprague-Dawley rats. The lenses were incubated in 24-well cluster dishes in modified TC-199 medium and were placed in a 37° C. incubator with a 95% air/5% $CO_2$ atmosphere. The lenses were incubated in 2 ml of culture medium, which was adjusted to 300 milliosmoles (mOsm). Lenses were incubated, for 1 to 24 hours, in the culture medium with 4.0 mM tempol-H, or with 4.0 mM of the oxidized form, tempol. At the appropriate time, the lenses were removed from the medium, blotted dry, homogenized and were analyzed for active compound by electron spin resonance method (ESR). In one experiment, lenses were incubated for 4 hours and dissected into epithelial, cortical and nuclear sections before analysis.

Results: Concentrations (mM, in lens water) of tempol-H reached 0.4 mM, 0.8 mM and 1.0 mM, respectively, after 1, 2 and 4 hours incubation of active compound. Levels of tempol-H found, after incubation of lenses with the oxidized form tempol, reach 0.6 mM, 1.5 mM and 2.8 mM respectively. In the latter case, only a trace (5% or less) of the oxidized form tempol, was found in the lens; it was almost completely converted to the reduced form tempol-H.

Distribution of tempol-H between the lens epithelium, cortex and nucleus was fairly even, after a 4-hour incubation period with tempol-H. Levels of tempol-H reached 1.5 mM, 0.8 mM and 1.0 mM, respectively, in the epithelium, cortex and nucleus. Levels of tempol-H/tempol in lenses incubated with the oxidized form, tempol, were 1.2 mM, 2.9 mM and 2.0 mM, respectively. In the latter case, all compounds in the nucleus were in the reduced form with only about 5% in the epithelium in the oxidized form.

Conclusion: Both the reduced and oxidized forms of the active agent readily penetrated into the cultured rat lens from the bath medium and distributed to the epithelium, cortex and nucleus. Incubation of lenses with the oxidized form tempol, results in high concentrations of reduced compound tempol-H throughout the lens.

Example 3

1-oxyl-4-(3'-ethoxy-2',2'-dimethyl)propanecarbonyloxy-2,2,6,6-tetramethylpiperidine]

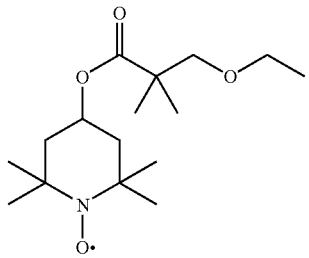

undec-7-ene (DBU) (800 mg, 5.26 mmol) and continue heating for 12 h. The reaction mixture was concentrated under reduced pressure. The residue was dissolved in ethyl acetate (100 mL) and was washed successively with 1N HCl, saturated NaHCO₃ and brine, was dried over anhydrous sodium sulfate and was concentrated in vacuo to give red colored solid (1.48 g). This was purified by column chromatography on silica gel using cyclohexane:ethyl acetate (8:1) as eluent to give a red colored crystalline solid (1.22 g, 70.0%).

IR (KBr, cm-1): 1360 (N—O.), 1725 (ester)

Example 4

1-hydroxy-4-(3'-ethoxy-2',2'-dimethyl)propanecarbonyloxy-2,2,6,6-tetramethylpiperidine Hydrochloride

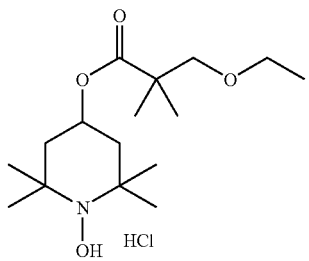

The nitroxide of Example 2 (1.02 mg, 3.34 mmol) was added to a solution of saturated hydrogen chloride in ethanol (20 mL). The red color disappears quickly and the resulting yellow colored solution was boiled to give a clear colorless solution. The solution was concentrated in vacuo, was dissolved in 100 mL ethyl acetate and was washed with saturated NaHCO₃ to obtain the hydroxylamine free-base. The ethyl acetate layer was separated and concentrated to give a red colored oil which was mostly nitroxide, by TLC. This oil was purified by column chromatography on silica gel using cyclohexane:ethyl acetate (4:1) as eluent to give a red colored crystalline solid (700 mg). The solid was dissolved in a solution of saturated hydrogen chloride in ethanol (20 mL), was concentrated in vacuo, and was recrystallized from ethyl acetate:diisopropylether (2:1, 50 mL) to give white crystalline solid (320 mg). m.p.140-142° C. (dec.).

$^1$H-NMR (270 MHz, D₂O) ppm: 1.48 (6H, s); 1.57 (3H, t); 1.63 (12H, s); 1.82 (2H, s); 2.02 (2H, t); 2.40 (2H, d), 3.88 (2H, q); 5.44 (1H, m)

IR (KBr, cm-1): 3487 (OH), 1726 (ester)

Mass Spec. (EI, m/z) 301 (M+)

Example 5a 1-oxyl-4-cyclopropanecarbonyloxy-2,2,6,6-tetramethylpiperidine

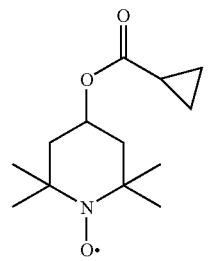

A suspension of sodium hydride (60% in oil, 1.0 g, 25 mmol) in dry THF (50 mL) was stirred at room temperature for 5 min and to this mixture was added tempol (4.0 g, 23 mmol). The mixture was stirred for 1 h, cyclopropanecarbonyl chloride (2.4 g, 23 mmol) was added dropwise over 5 min and then it was refluxed for 1 h. The reaction mixture was concentrated under reduced pressure. The residue was taken up in pentane (100 mL) and the supernatant was separated and concentrated under reduced pressure to give red solid. This solid was purified by column chromatography on silica gel using cyclohexane:ethyl acetate (3:1) as eluent to give a red colored crystalline solid (1.4 g, 5.8 mmol, 25.3%).

IR (KBr, cm-1): 1361 (N—O.), 1720 (ester)

Example 5b

Alternative Method—1-oxyl-4-cyclopropanecarbonyloxy-2,2,6,6-tetramethylpiperidine

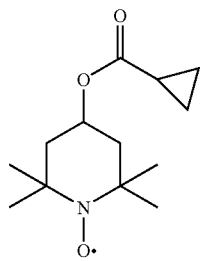

1,1'-Carbonyldiimidazole (1.78 g, 11 mmol) was added in small portions to a stirred solution of cyclopropanecarboxylic acid (860 mg, 10 mmol) in dry DMF (10 mL). A vigorous gas evolution was observed. This solution was heated at 40° C. for 1 h. To this mixture was then added tempol (1.72 g, 10 mmol) and 1,8-diazabicyclo[5,4,0]undec-7-ene(DBU) (1.52 g, 10 mmol) and it was heated at 40° C. for another 12 h. The reaction mixture was concentrated under reduced pressure. The residue was dissolved in ethyl acetate (100 mL) and was washed successively with 1N HCl, saturated NaHCO$_3$ and brine. The ethyl acetate layer was separated, dried over anhydrous sodium sulfate and concentrated in vacuo to give red colored solid. This solid was purified by column chromatography on silica gel using cyclohexane:ethyl acetate (8:1) as eluent to give a red colored crystalline solid (720 mg, 30.0%).

IR (KBr, c m$^{-1}$): 1360 (N—O.), 1720 (ester)

Example 5c

Alternative Method—1-oxyl-4-cyclopropanecarbonyloxy-2,2,6,6-tetramethylpiperidine [DCC/DMAP Esterification Method]

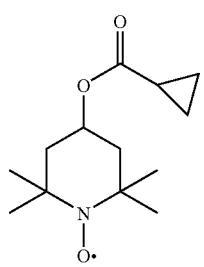

To a stirred solution of tempol (1.72 g, 0.01 mmole), cyclopropanecarboxylic acid (0.946 g, 0.011 mmole), and DMAP (0.12, 0.001 mmole) in dichloromethane (25 ml) was added DCC (2.27 g, 0.11 mmole) and the mixture was stirred overnight at room temperature. The mixture was filtered over celite and the solution was evaporated under reduced pressure. The product was isolated by silica gel column chromatography using first hexane and then 10% ethyl acetate in hexane. Yield: 2.26 g (94.1). IR and NMR were consistent with the assigned structure.

Example 6

1-hydroxy-4-cyclopropanecarbonyloxy-2,2,6,6-tetramethylpiperidine Hydrochloride (Compound 1)

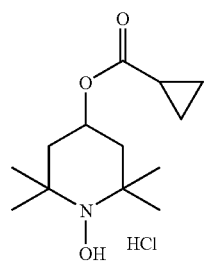

The nitroxide of Example 5a (2.2 g, 9.15 mmol) was added to a solution of saturated hydrogen chloride in ethanol (20 mL). The red color disappeared quickly and the resulting yellow colored solution was boiled to give clear colorless solution. The solution was concentrated in vacuo, dissolved in 100 mL ethyl acetate and was washed with saturated NaHCO$_3$ to obtain the hydroxylamine free-base. The ethyl acetate layer was separated, acidified with ethereal HCl, and concentrated to give white solid, which was recrystallized from ethanol (10 mL) as a white crystalline solid 1.15 g (4.13 mmol, 45.1%). m.p. 224-228° C. (dec.).

$^1$H-NMR (270 MHz, D$_2$O) ppm: 0.97 (4H,d); 1.43 (1H, m); 1.44 (6H, s), 1.46 (6H,s); 1.90 (2H,t); 2.28 (2H,t); 5.2 (1H,m)

IR (KBr, cm-1): 3478 (OH), 1720 (ester)

Mass Spec. (EI, m/z) 240 (M+)

Example 7

1-hydroxy-4-cyclopropanecarbonyloxy-2,2,6,6-tetramethylpiperidine Hydrochloride (Alternate Method)

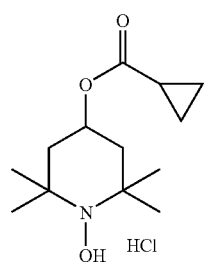

The nitroxide of Example 5a (700 mg, 2.91 mmol) was added to a solution of saturated hydrogen chloride in ethanol (20 mL). The red color disappeared quickly and the resulting yellow colored solution was boiled to give a clear colorless solution. The solution was concentrated in vacuo, dissolved in 100 mL ethyl acetate and concentrated to half volume to give a white crystalline solid, 627 mg (2.25 mmol, 77.5%.). m.p. 224-227° C. (dec.).

¹H-NMR (270 MHz, D₂O) ppm: 0.97 (4H,d); 1.43 (1H, m); 1.44 (6H, s), 1.46 (6H,s); 1.90 (2H,t); 2.28 (2H,t); 5.2 (1H,m)

IR (KBr, cm-1): 3476 (OH), 1720 (ester)

Mass Spec. (EI, m/z) 240 (M+)

Example 8

1-oxyl-4-(3'-benzyloxy-2',2'-dimethyl)propanecarbonyloxy-2,2,6,6-tetramethylpiperidine

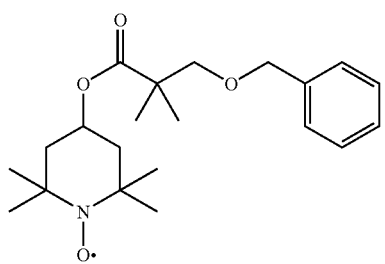

To a stirred solution of 3-benzyloxy-2,2-dimethylpropionic acid (1.04 g, 5 mmol), (prepared by a method similar to that described in J. Org. Chem., 38, 2349, 1975), in dry DMF (5 mL), was added, 1,1'-carbonyldiimidazole in small portions. A vigorous gas evolution was observed. This solution was heated at 50° C. for 30 min. To this mixture was then added tempol (900 mg, 5.23 mmol) and 1,8-diazabicyclo[5,4,0]undec-7-ene(DBU) (800 mg, 5.26 mmol). The mixture was heated at 50° C. for 3 days (monitored by TLC) and then it was concentrated under reduced pressure. The residue was dissolved in ethyl acetate (100 mL), washed successively with 1N HCl, saturated NaHCO₃ and brine, and dried over anhydrous sodium sulfate. The dried solution was concentrated in vacuo to give red colored solid (1.48 g). This solid was purified by column chromatography on silica gel using cyclohexane:ethyl acetate (3:1) as eluent to give a red colored crystalline solid (1.02 g, 2.8 mmol, 56.2%).

IR (KBr, cm-1): 1359 (N—O.), 1732 (ester)

Example 9

1-hydroxy-4-(3'-benzyloxy-2',2'-dimethyl)propanecarbonyloxy-2,2,6,6-tetramethylpiperidine Hydrochloride

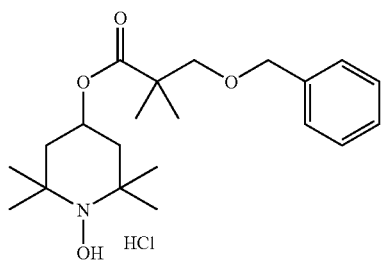

The nitroxide of Example 8 (1.02 mg, 3.34 mmol) was added to a solution of saturated hydrogen chloride in ethanol (20 mL). The red color disappears quickly and the resulting yellow colored solution was boiled to give clear colorless solution. The solution was concentrated in vacuo and the residue dissolved in ethyl acetate (20 mL). Hexane (20 mL) was added and product began to oil out; the mixture was then allowed to stand for 12 h. An oily residue was obtained by decantation of the solvent and it was treated with was isopropyl ether and warmed. Upon cooling the mixture, a waxy solid was obtained and recrystallized from ethyl acetate to give white crystalline solid (0.6 g, 1.5 mmol, 45%).

¹H-NMR (270 MHz, D₂O) ppm: 1.26 (6H, s), 1.51 (6H, s); 1.65 (6H, s); 2.01 (2H, t); 2.44 (2H, d), 5.40 (1H, m); 3.46 (2H, s), 4.55 (2H, S), 7.31 (5H, s)

IR (KBr, cm-1): 3480 (OH), 1712 (ester), 710 (aromatic)

Mass Spec. (EI, m/z) 262 (M+)

Example 10

1-hydroxy-4-(3'-hydroxy-2',2'-dimethyl)propanecarbonyloxy-2,2,6,6-tetramethylpiperidine Hydrochloride

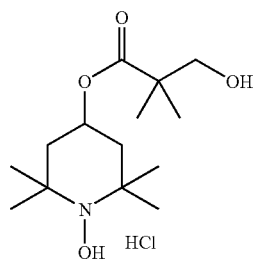

Pd/C (5%, 100 mg) was added to a solution of 1-oxyl-4-(3'-benzyloxy-2',2'-dimethyl)propanecarbonyloxy-2,2,6,6-tetramethylpiperidine (1.0 g, 3.83 mmol) in ethanol, and the mixture was hydrogenated in a Paar hydrogenation apparatus at 45 psi for 12 h. The reaction mixture was filtered through celite and concentrated in vacuo to give a clear colorless oil, which was purified by column chromatography on silica gel using cyclohexane:ethyl acetate (3:1) as eluent to give a colorless oil. The oil was dissolved in a solution of saturated hydrogen chloride in ethanol (20 mL) and concentrated in vacuo. Product crystallized upon standing, and was recrystallized from ethanol (123 mg, 0.4 mmol, 10.4%). m.p. 210-215° C. (dec.).

¹H-NMR of the free base (270 MHz, CDCl₃) ppm: 1.14 (6H, s), 1.44 (6H, s); 1.57 (6H, s); 1.70 (2H, m); 2.8 (1H, s, br), 3.65 (2H, s) 5.16 (1H, m)

IR (KBr, cm-1): 3480 (OH), 1712 (ester), 710 (aromatic)

Mass Spec. (EI, m/z) 262 (M+)

Example 11

1-oxyl-4-(1-methyl-cyclopropane)carbonyloxy-2,2,6,6-tetramethylpiperidine

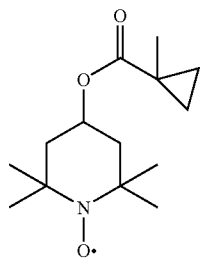

A suspension of sodium hydride (60% in oil 2.2 g), in dry THF (80 mL) was stirred at room temperature for 5 min and then tempol (3.0 g, 17.44 mmol) was added. The mixture was stirred for 30 min, 1-methyl-cyclopropanecarbonyl chloride (2.2 g, 18.71 mmol) was added drop wise over 5 min and then it was refluxed for 12 h. The reaction mixture was concentrated under reduced pressure and the residue crystallized immediately. The product was purified by column chromatography on silica gel using cyclohexane:ethyl acetate (3:1) as eluent to give a red colored crystalline solid (2.0 g, 7.86 mmol, 45.1%).

IR (KBr, cm-1): 1314 (N—O.), 1722 (ester)

Example 12

1-hydroxy-4-(1-methyl-cyclopropane)carbonyloxy-2,2,6,6-tetramethylpiperidine Hydrochloride

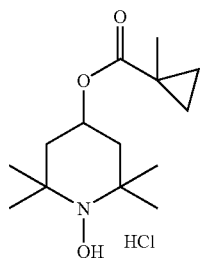

The nitroxide of Example 11 (700 mg, 2.91 mmol) was added to a solution of saturated hydrogen chloride in ethanol (10 mL). The red color disappears quickly and the resulting yellow colored solution was boiled to give a clear colorless solution. The solution was concentrated in vacuo to give white crystalline solid, which was filtered, washed with ethyl acetate and dried in vacuo (0.700 mg, 2.4 mmol, 82.7%) m.p. 215° C.-220° C. (dec.).

$^1$H-NMR (270 MHz, D$_2$O) ppm: 0.80 (2H, d); 1.19 (2H, m); 1.21 (2H,s); 1.44 (15H, s); 2.03 (4H, m); 5.10 (11H, m)

Mass Spec. (EI, m/z) 254 (M+)

Example 13

1-oxyl-4-(2-furan)carbonyloxy-2,2,6,6-tetramethylpiperidine

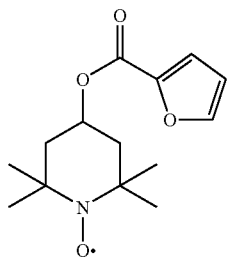

A stirred mixture of sodium methoxide (25% sodium methoxide in methanol, 200 mg) in benzene (100 mL) was heated to reflux and the benzene was gradually distilled off to half volume to obtain a fine suspension of solid sodium methoxide. To this mixture was added tempol (1.76 g, 10 mmol), methyl 2-furoate (1.26 g, 10 mmole) and benzene (50 mL). Distillation of benzene was continued for 8 h to remove formed methanol. The volume of benzene in the flask was maintained by adding more benzene. The benzene layer was washed with 1 N HCl, then with water, dried over anhydrous sodium sulfate and evaporated to dryness to give a red solid (1.72 g), which was recrystallized from hexane to give 1.45 g of product. It was further purified by column chromatography on silica gel using cyclohexane:ethyl acetate (3:1) as eluent to give a red colored crystalline solid (1.02 g, 3.82 mmol, 32.8%).

IR (KBr, cm-1): 1364 (N—O.), 1716 (ester), 706 (aromatic)

Example 14

1-hydroxy-4-(2'-furan)carbonyloxy-2,2,6,6-tetramethylpiperidine Hydrochloride

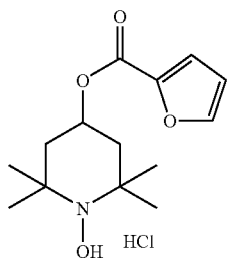

The nitroxide of Example 13 (300 mg, 1.13 mmol) was added to a solution of saturated hydrogen chloride in ethanol (10 mL). The red color disappeared quickly and the resulting yellow colored solution was boiled to give clear colorless solution. The solution was kept at room temperature for 1 h and a white crystalline solid separated. It was filtered, washed with ethyl acetate and dried in vacuo to afford the hydroxylamine (220 mg, 0.72 mmol, 64.5%, m.p. 209.4° C.-210.4° C.).

$^1$H-NMR (270 MHz, D$_2$O) ppm: 1.49 (6H, s); 1.62 (6H, s); 2.03 (2H, t); 2.42 (2H, d), 5.49 (1H, m); 6.63 (1H, q); 6.64 (1H, d), 7.34 (1H, d), 7.74 (1H, s)

Mass Spec. (EI, m/z) 266 (M+)

Example 15

1-oxyl-4-(3'-tetrahydrofuran)carbonyloxy-2,2,6,6-tetramethylpiperidine

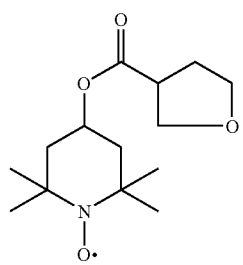

To a stirred solution of 3-tetrahydrofuancarboxylic acid (1.5 g, 13 mmol) in dry DMF (20 mL) was added 1,1'-carbonyldiimadazole (2.3 g, 14.18 mmol) in small portions. A vigorous gas evolution was observed. This solution was heated at 70° C. for 1 h. To this mixture was then added tempol (2.23 g, 12.97 mmol) and 1,8-diazabicyclo[5,4,0]undec-7-ene(DBU) (2.0 g, 13.14 mmol) and heating was continued for 12 h. The reaction mixture was poured into 250 mL water and extracted with ether (2×100 mL). The ethereal layers were combined and washed successively with 1N HCl, saturated NaHCO$_3$ and brine, dried over anhydrous sodium sulfate and concentrated in vacuo to give red colored solid (2.05 g), that recrystallized from ethyl acetate:Hexane (1:2) to obtain pure red crystalline solid nitroxide (1.45 g, 5.36 mmol, 37.8%).

IR (KBr, cm$^{-1}$): 1360 (N—O.), 1725 (ester)

Example 16

1-hydroxy-4-(3'-tetrahydrofuran)carbonyloxy-2,2,6,6-tetramethylpiperidine Hydrochloride

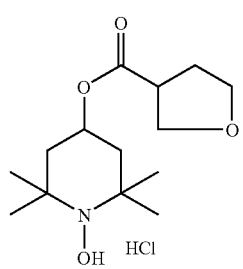

The nitroxide of Example 15 (300 mg, 1.11 mmol) was added to a solution of saturated hydrogen chloride in ethanol (10 mL). The red color disappeared quickly and the resulting yellow colored solution was boiled to give a clear colorless solution. The solution was kept at room temperature for 1 h and a white crystalline solid separated. The solid was filtered, washed with ethanol and dried in vacuo to afford product (146 mg, 0.48 mmol, 42.86%, m.p. 221.0° C.-223.2° C.).

$^1$H-NMR (270 MHz, DMSO-d$_6$) ppm: 0.84 (2H, m); 0.90 (2H, m); 1.35 (6H, s); 1.46 (6H, s); 1,65 (1H, m); 2.13 (2H, t); 2.44 (2H, d), 5.14 (1H, m)

Example 17

Absorption of Representative Compounds Across the Corneas of Animals

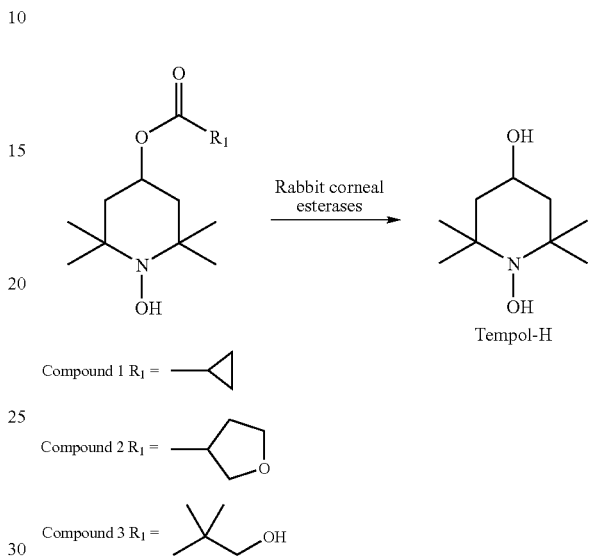

Groups of six New Zealand White rabbits were used in the study to evaluate the absorption of tempol-H and compound 1. The test compounds were prepared in sterile saline solutions at a concentration of 3.5% weight by volume. The animals were held in restraining boxes during instillation of eye drops, 50 μL in each eye, using a micropipette. After dosing, the eye was gently held closed for 60 seconds. The rabbits were dosed twice daily for 4 consecutive days. On the fifth day, rabbits were dosed once and then euthanized at 30 minutes post dose (2 rabbits), 60 minutes post-dose (2 rabbits) and at 120 minutes post-dose (2 rabbits). Immediately after euthanization, aqueous humor was collected from each rabbit. The aqueous concentration of tempol-H in each sample was measured using the electron spin resonance (ESR) method.

Aqueous humor levels of tempol-H after dosing with tempol-H, were below detectable limits of the assay at all time points (see FIG. 1). Aqueous humor concentrations of tempol-H after dosing with compound 1 were maximal at 30 minutes post-dose but were still present at 2 hours post-dose. (see FIG. 1 and Table 1).

TABLE I

Aqueous Humor Concentrations: Absorption Studies in Rabbits
Dose: 50 μL of 3.5% solution, single dose (N = 4 eyes/timepoint)
Concentration of Tempol-H μM

| | | 30 minutes | 60 minutes | 120 minutes |
|---|---|---|---|---|
| Compound 1 | | 51.0 | 20.0 | 1.5 |
| | | 30.0 | 30.0 | 1.2 |
| | | 18.0 | 6.0 | 7.0 |
| | | 30.0 | 3.0 | 8.0 |
| Mean | | 32.3 | 14.8 | 4.4 |
| μg/ml | | (5.5) | (2.5) | (0.75) |

Example 18

Identification of Metabolites of Compound 1 in Rabbit Eye

Aqueous humor samples, from the in vivo rabbit study described in Example 16 were identified by GC/MS for the presence of compound 1 and its metabolites, tempol-H and carboxylic acid ($R_1COOH$), formed by hydrolysis of compound 1 by ocular esterases. Both the metabolites were observed but not Compound 1. This confirmed that Compound 1 was completely converted to its metabolites.

A sample of aqueous humor was freeze dried in a 10 mL amber colored glass vial containing a tiny magnetic bar. To this was added 1 mL of methylene chloride and the solution was stirred for two minutes and allowed to stand for five minutes. A 3 µL aliquot of the methylene chloride layer was injected into the GC column. The cyclopropanecarboxylic acid was detected by a mass spectrometer detector at 13.02 (retention time) with m/z=85 (GC model 5989B and MS model 5890 series II (both made by HP)). Agilent DB-5 column 25 m length, 0.2 mm diameter was used. Carrier gas He at 22 cm/sec. Inlet temperature was 250° C., detector 280° C. For every injection, the temperature was held at 35° C. for 5 minutes, then was increased to 240° C. at 10° C./min, and was held at 240° C. for 3 minutes. Splitless injection was used.

Example 19

Tolerance of Compound 1 in Vivo in Rabbit Eyes

Eyedrops containing 3.5% compound 1 were administered six times, at 1-hour intervals, to each eye of two conscious rabbits. The drug was well tolerated and no adverse findings were noted in this preliminary study.

Example 20

Ocular Bioavailability in Rabbit

The ocular bioavailability of compounds 2 and 3 was evaluated in New Zealand White rabbits. Each compound was dissolved in 10 mM phosphate buffer, pH 7.0 to a concentration of 125 mM. This concentration was equal to ~3.5% for compounds 2 and 3. Fifty µl was instilled onto the cornea of both eyes of each rabbit 6 times at 1-hour intervals. Two rabbits were used for each compound. One rabbit treated with each compound was euthanized 30 minutes after the last dose and the second was euthanized 90 minutes after the final dose.

After death, the eyes of each rabbit were immediately enucleated and a blood sample was collected from the orbit. Aqueous humor was collected from each eye with a syringe and then the lens was dissected from the eye. The capsule/epithelium was carefully separated from the fiber mass and both parts were frozen on dry ice, the capsule/epithelium in 100 µl of 5 mM DTPA (diethylenetriaminepentaacetic acid) solution and the fiber mass in a sealed vial without added liquid. Likewise, the aqueous and blood samples were quick frozen. The rest of each eye including the cornea, retina, sclera and vitreous were frozen for possible future dissection and analysis. All samples were transported to the lab on dry ice and were stored at −75° C. until processed.

The aqueous concentration of tempol-H in each sample was measured using the electron spin resonance (ESR) method. Analysis of the aqueous humor reveals that both compounds penetrated the cornea and entered the aqueous chamber. The highest concentrations for both compounds was present in the 30-minute sample with the 90-minute samples being significantly reduced in concentration. Small amounts (2-3 µM of each compound) were also detected in the blood.

Example 21

Aqueous Humor Concentrations of Compounds 2 and 3; in Rabbits

TABLE II

Dose of Compound 2 and 3: 50 µL of 125 mM solution, at hourly intervals × 6 (N = 2 eyes/timepoint)
Concentration of Tempol-H µM

|            | 30 minutes | 90 minutes | Blood |
|------------|------------|------------|-------|
| Compound 3 | 31.4       | 11.6       | 2.3   |
|            | 22.2       | 9.0        | 2.5   |
| Mean       | 26.8       | 10.8       | 2.4   |
| µg/ml      | (4.6)      | (1.9)      | (0.4) |
| Compound 2 | 52.4       | 6.0        | 3.6   |
|            | 35.2       | 5.7        | 0.6   |
| Mean       | 43.8       | 5.9        | 2.1   |
| µg/ml      | (7.5)      | (1.0)      | (0.4) |

Example 22

Aqueous Solubility Data

TABLE III

Solubility of Compound of Example 6 was determined at room temperature in various systems.

| Conditions | Solubility mg/ml | Solubility % w/v |
|------------|------------------|------------------|
| Water | 74.9 | 7.5 |
| 0.9% Sodium chloride | 40.5 | 4.1 |
| 0.01 M Acetate buffer at pH 4.8 | 68.6 | 6.9 |
| 0.01 M Citrate buffer at pH 4.8 | 71.1 | 7.1 |
| Water + 1% w/v glycerin | 62.2 | 6.2 |
| Water + 1% w/v propylene glycol | 63.8 | 6.4 |

Similarly, the solubility compounds of Examples 10 and 16 in water were determined to be >3.5% w/v (>35 mg/ml) in water whereas the compound of Example 12 is soluble at approximately 0.1% w/v in water.

TABLE IV
Partition Coefficient of Ester Compounds
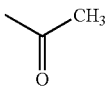
| Examples | R | Calculated PC |
|---|---|---|
| 23 | H | 0.8 |
| 24 | 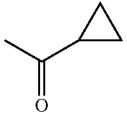 | 7.2 |
| 25 | 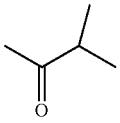 | 16.2 |
| 26 | 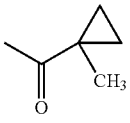 | 50.1 |
| 27 | 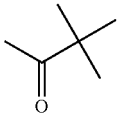 | 53.7 |
| 28 | 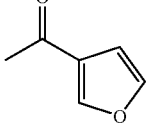 | 125.9 |
| 29 | 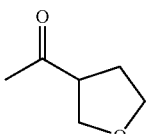 | 91.2 |
| 30 | 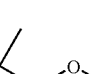 | 6.3 |
| 31 | 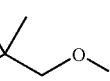 | 114.8 |
| 32 | 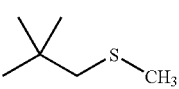 | 34.7 |
| 33 | 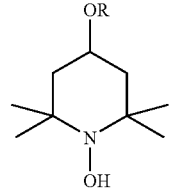 | 199.5 |
TABLE IV-continued
Partition Coefficient of Ester Compounds
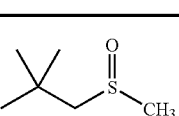
| Examples | R | Calculated PC |
|---|---|---|
| 34 | 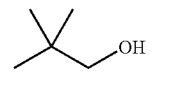 | 4.3 |
| 35 | 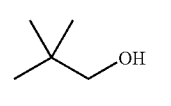 | 8.1 |
| 36 | 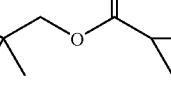 | 144.5 |
| 37 | 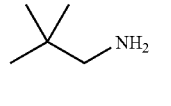 | 10 |
| 38 | 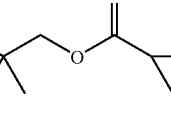 | 51.3 |
| 39 | 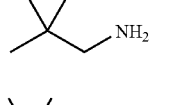 | 575.4 |
| 40 | 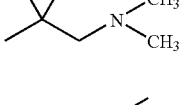 | 34.7 |
| 41 | 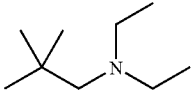 | 69.4 |
| 42 | 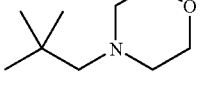 | 67.6 |
| 43 | 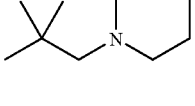 | 39.8 |

TABLE V
Melting Points of Ester Compounds

| Examples | R1 | R2 | M.P. (° C.) |
|---|---|---|---|
| 44 | O | cyclopropyl | 97.2-98.2 |
| 44 | OH (as HCl salt) | cyclopropyl | 224-228° C. (dec.). |
| 45 | OH (as HCl salt) | cyclopropyl | 224-227° C. (dec.). |
| 46 | O | 2-furyl | 103.9-105.2 |
| 47 | OH (as HCl salt) | 3-furyl | 209.4-210.1 |
| 48 | O | 4-(dimethylamino)phenyl | 150-152.3 |
| 49 | OH (as HCl salt) | 4-(dimethylamino)phenyl | 250.6-253.2 |
| 50 | O | 4-(acetoxy)phenyl | 64.8-66.1 |
| 51 | OH (as HCl salt) | 4-(acetoxy)phenyl | 229.0-230.9 |
| 52 | O | 4-hydroxyphenyl | 107-109.3 |
| 53 | OH (as HCl salt) | 4-hydroxyphenyl | 220.0-223.0 |
| 54 | O | 4-methoxyphenyl | 111.1-112.3 |
| 55 | OH (as HCl salt) | 4-methoxyphenyl | 228.0-231.2 |

TABLE V-continued
Melting Points of Ester Compounds

| Examples | R1 | R2 | M.P. (° C.) |
|---|---|---|---|
| 56 | O | 3,4,5-trimethoxyphenyl | 121.2-122.9 |
| 57 | OH (as HCl salt) | 3,4,5-trimethoxyphenyl | 241.8-244.6 |
| 58 | O | 2-hydroxy-(propenyl)phenyl | 145.2-146.4 |
| 59 | OH (as HCl salt) | 2-hydroxy-(propenyl)phenyl | 237.8-269.1 |
| 60 | O | phenyl propyl ketone | 132-133.0 |
| 61 | OH (as HCl salt) | phenyl propyl ketone | 267.9-270 |
| 62 | O | cyclobutyl | 68.3-69.9 |
| 63 | OH (as HCl salt) | cyclobutyl | 264.8-266.3 |

Spectral Data for the Ester Compounds $^1$H-NMR (270 MHz, DMSO-$d_6$) ppm: spectral data that was common to all 4-substituted-1-hydroxy-2,2,6,6-tetramethylpiperidine hydrochloride portion 1.35 (6H, s); 1.46 (6H, s); 2.13 (2H, t); 2.44 (2H, d), 5.14 (1H, m)

| Examples | IR CKBr) cm−1 Carbonyl(s) | $^1$H-NMR (270 MHz, DMSO-$d_6$) ppm: for the ester moiety |
|---|---|---|
| 57 | 1716 | 3.75(S, 9H); 6.95(s, 2H) |
| 61 | 1738 | 2.79(t, 2H); 3.31(t, 2H); 7.45(m, 2H); 7.55 |
|  | 1687 | (m, 1H); 7.93(d, 2H) |
| 53 | 1682 | 6.87(d, 2H); 7.83(d, 2H), 10.3(br, s, 1H) |
| 51 | 1718 | 3.9(s, 3H), 7.18(d, 2H), 8.07(d, 2H) |
|  | 1755 |  |
| 59 | 1723 | 6.54, 7.85(dd, J=16.0 Hz); 6.84(m, 1H); 7.24(m, 1H); 7.54(d, 1H); 7.86(d, 1H); 10/2(br, s, 1H) |
| 61 | 1718 | 1.96(m, 2H); 2.30(m, 4H); 2.78(m, 2H) |
| 49 | 1688 | 2.88(S, 6H); 6.65(d, 2H); 7.73(d, 2H) |
| 53 | 1682 | 3.70(s, 3H); 7.20(d, 2H); 7.72(d, 2H) |

The following Tables VI to XII describe methods used in the synthesis of additional examples of the ester compounds of the invention. The appropriate carboxylic acid listed in the Tables is converted to the ester nitroxide by the DCC/DMAP esterification method of Example 5c. The ester nitroxide is converted to the corresponding 1-hydroxypiperidine by the methods described in Examples 6 and 7.

3-acyloxy-2.2-dimethylpropionic acids were prepared by the method described in U.S. Pat. No. 4,851,436, the content of which is incorporated herein by reference, for the synthesis of 3-acetoxy-2,2-dimethylpropionic acid.

TABLE VI

Substitute cyclopropanecarboxylic acid with following compounds in DCC/DMAP esterification method:

| Examples | Starting material (structure) | Chemical name |
|---|---|---|
|  | [structure] | 3-Acetoxy-2,2-dimethylpropionic acid |
|  | [structure] | 3-Pivaloloxy-2,2-dimethylpropionic acid |
|  | [structure] | 3-Cyclopropane-carbonyloxy-2,2-dimethylpropionic acid |
|  | [structure] | 3-(1-Methyl-cyclopropanecarbonyloxy)-2,2-dimethylpropionic acid |
|  | [structure] | 3-(2-Methyl-cyclopropanecarbonyloxy)-2,2-dimethylpropionic acid |

TABLE VI-continued

Substitute cyclopropanecarboxylic acid with following compounds in DCC/DMAP esterification method:

| Examples | Starting material (structure) | Chemical name |
|---|---|---|
|  | [structure] | 3-(2,2-Dimethyl-cyclopropanecarbonyloxy)-2,2-dimethylpropionic acid |
|  | [structure] | 3-(3-Tetrahydro-furancarbonyloxy)-2,2-dimethylpropionic acid |
| 64 | [structure] | 3-(1-Methyl-3-tetrahydrofurancarbonyloxy)-2,2-dimethylpropionic acid |

TABLE VII 3-alkoxy-2.2-dimethylpropionic acids and 3-alkoxyalkyl-2.2-dimethylpropionic acids were prepared by the method described in J. Org. Chem. 38, 2349 (1975).
Substitute cyclopropanecarboxylic acid with following compounds in the DCC/DMAP esterification method (Example 5c):

| Starting material (structure) | Chemical name |
|---|---|
| [structure] | 3-Methoxy-2,2-dimethyl-propionic acid |
| [structure] | 3-propoxy-2.2-dimethyl-propionic acid |
| [structure] | 3-isopropoxy-2.2-dimethyl-propionic acid |
| [structure] | 3-Cyclopropylmethoxy-2,2-dimethylpropionic acid |
| [structure] | 3-(2-Methoxy-ethoxy)-2,2-dimethylpropionic acid |
| [structure] | 3-Ethoxymethoxy-2,2-dimethylpropionic acid |

Substitute cyclopropanecarboxylic acid with following compounds in the DCC/DMAP esterification method (Example 5c):

TABLE VIII

3-N-substituted-2,2-dimethylpropionic acids are prepared by the method described in U.S. Pat. No. 5,475,013 to Talley et al., the content of which is incorporated herein by reference. Substitute cyclopropanecarboxylic acid with the following compounds in the DCC/DMAP esterification method (Example 5c):

| Starting material (structure) | Chemical name |
|---|---|
| (structure) | 3-Amino-2,2-dimethylpropionic acid |
| (structure) | 3-Dimethylamino-2,2-dimethyl-propionic acid |
| (structure) | 2,2-Dimethyl-3-piperidin-1-yl-propionic acid |
| (structure) | 2,2-Dimethyl-3-(4-oxo-piperidin-1-yl)-propionic acid |
| (structure) | 2,2-Dimethyl-3-thiomorpholin-4-yl-propionic acid |
| (structure) | 2,2-Dimethyl-3-(4-methyl-piperazin-1-yl)-propionic acid |
| (structure) | 3-Imidazol-1-yl-2,2-dimethyl-propionic acid |

TABLE IX

3-S-substitted-2,2-dimethylpropionic acids are prepared by the method described in U.S. Pat. No. 5,475,013. Substitute cyclopropanecarboxylic acid with following compounds in the DCC/DMAP esterification method (Example 5c):

| Starting material (structure) | Chemical name |
|---|---|
| (structure) | 2,2-Dimethyl-3-methyl-sulfanylpropionic acid |
| (structure) | 3-Methanesulfinyl-2,2-dimethylpropionic acid |
| (structure) | 2,2-Dimethyl-3-phenyl-sulfanylpropionic acid |
| (structure) | 3-Benzenesulfonyl-2,2-dimethylpropionic acid |

TABLE X

3-Substitted-2,2-dimethylpropionic acids are prepared by the method described in U.S. Pat. No. 5,475,013. Substitute cyclopropanecarboxylic acid with following compounds in the DCC/DMAP esterification method (Example 5c):

| Starting material (structure) | Chemical name |
|---|---|
| (structure) | 2,2-Dimethyl-3-phenylpropionic acid |
| (structure) | 2,2-Dimethyl-3-pyridin-4-yl-propionic acid |

TABLE XI

Various NSAID (nonsteroidal anti-inflammatory drugs containing carboxylic acid group) are commercially available. Substitute cyclopropanecarboxylic acid with following compounds in the DCC/DMAP esterification method:

| Starting material (structure) | Chemical name |
|---|---|
| (structure) | Ketorolac or 5-Benzoyl-2,3-dihydro-1H-pyrrolizine-1-carboxylic acid |
| (structure) | Flurbibrofen or 2-(2-Fluoro-biphenyl-4-yl)propionic acid |

TABLE XI-continued

Various NSAID (nonsteroidal anti-inflammatory drugs containing carboxylic acid group) are commercially available. Substitute cyclopropanecarboxylic acid with following compounds in the DCC/DMAP esterification method:

| Starting material (structure) | Chemical name |
|---|---|
|  | Ibuprofen or 2-(4-Isobutyl-phenyl)propionic acid |
|  | Naproxen or 2-(5-Methoxy-naphthalen-2-yl)propionic acid |
|  | Aspirin |

Various NSAID (nonsteroidal anti-inflammatory drugs containing carboxylic acid group) are commercially available. Substitute cyclopropanecarboxylic acid with following compounds in the DCC/DMAP esterification method:

TABLE XII

Various carboxylic acids are commercially available. Substitute cyclopropanecarboxylic acid with the following compounds in DCC/DMAP esterification method:

| Starting material (structure) | Chemical name |
|---|---|
|  | Cyclopent-3-enecarboxylic acid |
|  | But-3-enoic acid |
|  | Tetrahydro-furan-2-carboxylic acid |
|  | Tetrahydro-thiophene-2-carboxylic acid |
|  | Tetrahydro-thiophene-3-carboxylic acid |
|  | 2-Oxo-thiazolidine-4-carboxylic acid |
|  | 2-Oxo-oxazolidine-4-carboxylic acid |
|  | 2-Oxo-imidazolidine-4-carboxylic acid |
|  | 2-Oxo-[1,3]dioxolane-4-carboxylic acid |
|  | 1-Methyl-pyrrolidine-3-carboxylic acid |
|  | 1-methyl-pyrrolidine-2-carboxylic acid |
|  | Tetrahydro-pyran-4-carboxylic acid |
|  | Tetrahydro-thiopyran-4-carboxylic acid |
|  | 1-Methyl-piperidine-4-carboxylic acid |
|  | 3-hydroxy-2-methylpropionic acid |

TABLE XII-continued

Various carboxylic acids are commercially available. Substitute cyclopropanecarboxylic acid with the following compounds in DCC/DMAP esterification method:

| Starting material (structure) | Chemical name |
|---|---|
| HO₂C—⟨—NH₂ | 3-amino-2-methylpropionic acid |
| HO₂C—⟨—SH | 3-mercapto-2-methylpropionic acid |
| HO₂C—⟨—O— | 3-methoxy-2-methylpropionate (synthesis: U.S. Pat. No. 4,617,154, the content of which is incorporated herein by reference) |

Example 65

Pharmacokinetics, Ocular Tissue Distribution, and Urinary Excretion of Total Radioactivity Following Single Topical Dose Administration of Compound 1 in Rabbits. The pharmacokinetics, ocular tissue distribution and urinary excretion of total radioactivity following a single topical dose administration of the tritiated hydrochloride of Compound 1 in rabbits was evaluated. Eighteen male New Zealand White (Harlan) rabbits, age 3-6 months, weight 2.1 to 3.0 kg were utilized.

Experimental Design: The experimental design was a randomized, single-treatment study in one group of rabbits administered a single topical application of [³H]Compound 1-HCl into both eyes. The group consisted of 6 subgroups of 3 animals. At six specified times (0.5, 1, 2, 4, 8 and 24 hours) post-dose, three animals per subgroup were euthanized and terminal samples collected. Animals designated to the 24 hour post-dose subgroup were placed in metabolism cages and urine was collected from 0-12 and 12-24 hours post-dose. Terminal blood was collected by cardiac puncture technique. From each eye, the following ocular tissues were harvested: aqueous humor; vitreous humor; lens; and cornea. Total radioactivity was determined in all samples.

The design and dosages are shown in the table below.

| Group | #/Sex | Dose Volume Per Eye (ml) | Dose Level (mg/kg) | Dose Level (μCi/kg) | Dose Concn (mg/ml) | Dose Concn (mCi/ml) |
|---|---|---|---|---|---|---|
| 1 | 18/M | 0.04 | ~0.8 to 1.2 | ~34 to 49 | 30 | 1.275 |

Animals received a single topical ocular dose in each eye, right (OD) followed by left (OS). While slightly pulling away the lower eyelid from the globe, the dose was accurately pipetted onto the cornea and allowed to collect in the lower conjunctival sac. The eyelids were gently held shut for 1 minute after drug instillation and then carefully released.

Data analysis and statistical evaluation: Counts per minute for all assayed samples were converted to disintegrations per minute (DPM) using a Beckman LS6000 counter. Following appropriate background subtraction, DPM values were converted to concentrations (DPM per ml or g). Average DPM per ml or g values were calculated. Mean concentration values of $^3$H radioactivity were calculated and converted to equivalents per ml or g based on the measured specific activity and nominal concentration of the administered test article formulation as determined by oxidation. Concentrations of total radioactivity in blood and plasma, amount (% of dose) and concentration in ocular tissue and urine samples were determined. Elimination kinetics including blood, plasma, and tissue half-lives were calculated. Urinary excretion data were also tabulated. Statistical evaluation consisted of descriptive statistical analysis. Pharmacokinetics of radioactivity were evaluated by model independent analyses pending suitability of sample assay results. Non-truncated numerical values were used in the calculations.

Representative results: A single drop (40 ul) of a 3% solution of Compound 1 yielded the following peak tissue concentrations (nanogram equivalents/gram), at 30 minutes post-dose, in cornea, aqueous, lens, vitreous, blood and plasma, respectively:

| Cornea | Aqueous | Lens | Vitreous | Blood | Plasma |
|---|---|---|---|---|---|
| 13090 | 5930 | 310 | 150 | 240 | 360 |

Figure 2:
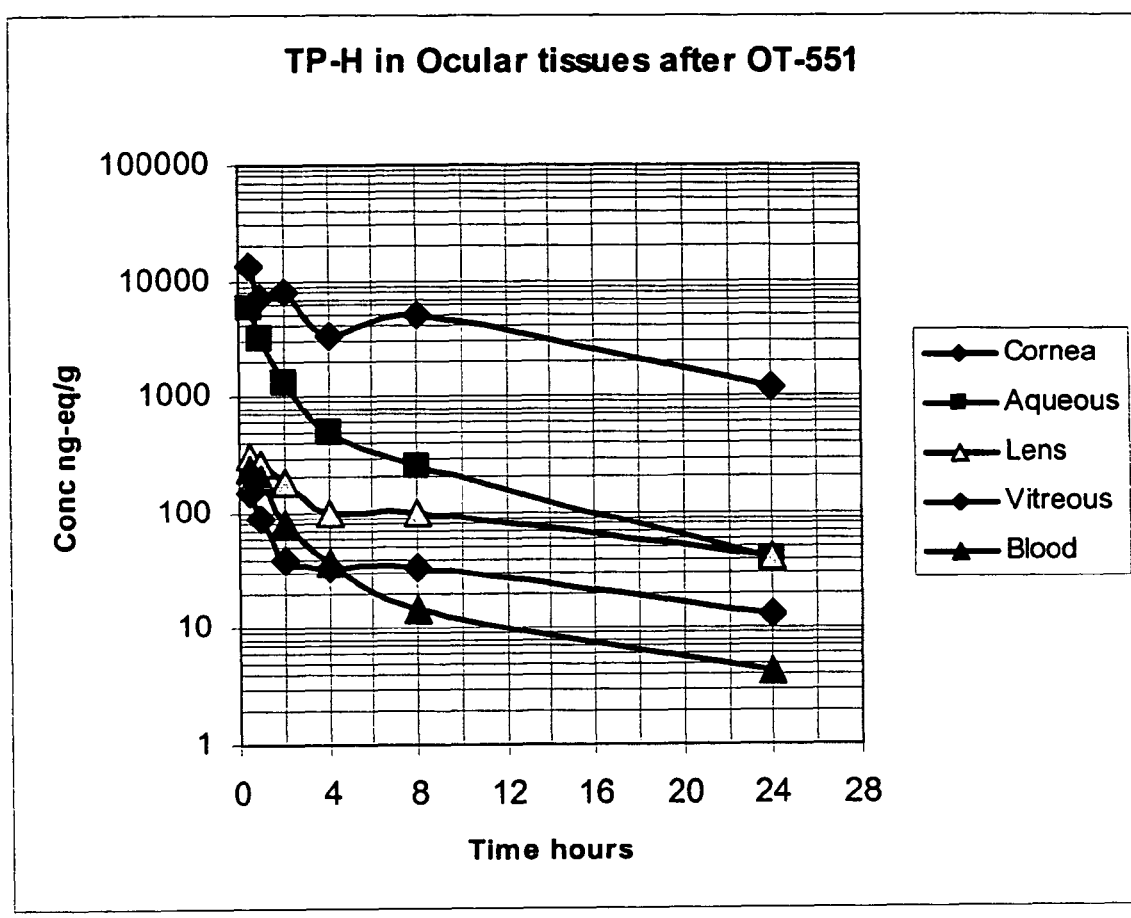
FIG. 2 depicts levels of tempol-H in various tissues of rabbit eyes following topical administration of Compound 1, at selected time points post-treatment.

As shown in FIG. 2, radioactivity was still measurable in all tissues at 24 hours post-dose. It was previously established that dosing rabbits with a 3% solution of Compound 1, 4 times daily, for one week caused no toxicity.

Example 66

Effect of Compound I or Tempol-H Treatment on Photochemical Retinal Injury in a Rabbit Model The ability of light to produce retinal injury well below the levels capable of producing thermal damage has been termed photochemical retinal injury. The mechanism of action for photochemical retinal injury is believed to be the light induced production of free radicals. The ability of commonly used light sources in clinical ophthalmology to produce photochemical retinal injury is well recognized. The operating microscopes used in ophthalmic surgery have been shown to have the capability of producing retinal photochemical injury. This observation has been utilized to produce a model in the rabbit eye to test the ability of various agents to block photochemical retinal injury. It has been determined that opthalmoscopically visible retinal lesions are detectable after as little as 2.5 minutes of exposure to an operating microscope. The protocol set forth below is utilized to determine whether Compound 1 or tempol-H given via intravitreal injection has the ability to block the development of an ophthalmoscopically visible photochemical retinal lesion produced by a operating microscope.

Materials and Methods: One week prior to treatment, a baseline Fundus photograph and FA is performed on each animal. One day prior to being exposed to the light from a operating microscope, one eye of each animal receives an intravitreal injection of 0.1 cc of BSS® as a control and the fellow eye receives 0.1 cc of Compound 1 or Tempo-H in a BSS®vehicle. The animals are anesthetized with a IM injection of a 60%-40% mixture of ketamine hydrochloride 100 mg/ml and Xylazine 20 mg/ml. A speculum is inserted into the eye receiving the injection, and the injection is performed using a 30 g needle passed through the sclera just behind the limbus and angled to clear the lens, placing the tip in the mid vitreous cavity. Following injection, the intraocular pressure is monitored using a hand-held Applanation tonometer. If necessary, a paracentesis is performed to return intraocular pressure to normal levels, prior to returning the animals to their cages. Alternatively, Compound 1 or tempol-H may be administered to the rabbit eye by multiple instillations of topical eye drops prior to the procedure.

Forty eyes in 20 pigmented rabbits are exposed to the light from a Zeiss model OpMi 1 operating microscope for various periods of time up to one hour. The rabbits are anesthetized with a IM injection of a 60%-40% mixture of ketamine hydrochloride 100 mg/ml and Xylazine 20 mg/ml. The rabbits are then positioned on a table; a lid speculum is inserted in the eye to be exposed. The pupil is dilated with tropicamide HCL 1%, and the cornea irrigated with BSS®. The light from the microscope is positioned 20 cm from the animal in a manner so that the light is centered and parallel to the eye. The light filaments are centered in sharp focus on the cornea. Forty-eight hours after exposure, the animals are examined and a repeat Fundus photograph and FA performed. The animals are killed using standard techniques and selected eyes are harvested and stored in chilled glutaldehyde solution, for additional analyses.

Example 67

Evaluation of Compound 1 or Tempol-H Incorporation into Retinal Tissue of Rabbits Following Intravitreous Injection To assess the efficacy of Compound 1 or tempol-H at preventing AMD and other retinal disorders, it must be determined that the drug is incorporated into retinal tissue. The protocol set forth in this example utilizes scintillation technique to establish quantity and duration of Compound 1 or tempol-H incorporation into retinal tissue following intravitreous injection in the rabbit. The New Zealand White Rabbit is well characterized in experiments involving intravitreous injection as the large eye of the rabbit provides a suitable template for treatment administration (Hosseini et al., 2003, Lasers Surg. Med. 32: 265-270). Furthermore, the New Zealand White Rabbit has been used extensively in experiments assessing drug uptake into retinal tissue via scintillation technique (Ahmed et al., 1987, J. Pharm. Sci. 76: 583-586).

Materials and Methods: Twenty-four New Zealand White Rabbits, all male, weighing between 2.5 and 3 kilograms, are used in this protocol. The rabbits are randomized into one of two treatment arms. Initially, rabbits are given baseline ocular exams to ensure that all eyes are free of irritation and infection. Following randomization and baseline exams, rabbits are anesthetized by subcutaneous injection of 100 mg/ml ketamine/20 mg/ml xylazine. One drop of commercially available 0.5% proparacaine hydrochloride is applied to both eyes. Rabbits are then treated bilaterally by intravitreous injection in accordance with the masked randomization scheme shown below.

Masked Treatment Arms:
1. Bilateral intravitreous injection with labeled Compound 1 or tempol-H. (N=12)
2. Bilateral intravitreous injection with placebo (vehicle). (N=12)

On Day 1, 7, 14 and 28, respectively, six rabbits, three from each treatment arm respectively, are sacrificed with a lethal dose of sodium pentobarbital. Immediately following sacrifice, bilateral enucleation is performed and the retinal tissue is removed for scintillation analysis (retinal tissue may be frozen following enucleation to prevent fluid loss). Retinal tissue is ground into a slurry and dissolved in an alkali or quaternary ammonium compound. Scintillation readings are conducted to quantify the amount of Compound 1 or tempol-H present in the retinal tissue.

For statistical analysis, data from all rabbits that are dosed with test articles is considered evaluable. Primary and secondary efficacy variables are for statistical significance. Two-sided nonparametric statistical tests are used, and $p<0.05$ is considered statistically significant.

Example 68

Efficacy of Tempol-H in Protection Against Photooxidative Processes in the Retinal Pigment Epithelium (RPE)

Background: Although the etiology of atrophic age-related macular degeneration (AMD) is not fully understood, it is generally accepted that AMD begins with the death of retinal pigment epithelial cells, the degeneration of photoreceptor cells, and resultant loss of vision, occurring thereafter. There is a growing body of evidence linking the lipofuscin that accumulates in RPE with the death of these cells. For instance, not only are lipofuscin levels highest in RPE cells underlying the macula, the monitoring RPE lipofuscin by detection of fundus autofluorescence has also shown that areas of RPE atrophy develop at sites of previously increased fluorescence. Studies concerned with examining associations between RPE lipofuscin and RPE cell death have shown that a major constituent of RPE lipofuscin, the bisretinoid fluorophore A2E, can perturb cellular membranes and can mediate blue light damage to RPE. The photoexcitation of A2E leads to the generation of singlet oxygen and the addition of the latter to carbon-carbon double bonds along the retinoid-derived side arms of A2E such that epoxides are formed. In this way, A2E is converted into a mixture of compounds (A2E-epoxides) bearing epoxides of varying numbers. These highly reactive epoxides have been shown to damage the cell. Ultimately, the photochemical events provoked by the irradiation of A2E in RPE cells initiates cell death by way of a pathway that involves the participation of cysteine-dependent proteases (caspases) to cleave cellular substrates and that is modulated by the mitochondrial protein bcl-2.

The ability of tempol-H to protect against A2E-mediated blue light damage was examined.

Materials and Methods: ARPE-19 cells that have accumulated A2E in culture were exposed to 430+/−20 nm light delivered from a halogen source. This wavelength of light is relevant since (i) the excitation maximum of A2E is approximately 430 nm, and (ii) light of this wavelength reaches the RPE in vivo while light of wavelengths longer than 400 nm are not absorbed by the cornea and lens. Cell death in blue light-illuminated A2E-laden RPE was compared with and without pre-treatment (24 hours) with tempol-H. The loss of cell viability was quantified by:

1. A calorimetric microtiter assay based on ability of healthy metabolically active cells to cleave the yellow tetrazolium salt MTT to purple formazan crystals. Cell viability was assessed 24 hours after blue light illumination. Triplicate wells were assayed in each of 2 experiments.
2. Two-color fluorescence assay in which the nuclei of all dead cells appear red due to staining by a membrane-impermeant dye (Dead Red nuclei acid stain, Molecular Probes) with the nuclei of all cells stained blue with DAPI. Cell viability was assessed 8 hours after blue light illumination. Replicates were assayed by counting cells within 5 microscopic fields within the area of illumination in each well and 3 wells were assayed per experiment. Data are based on of 3 experiments.

Figure 3:
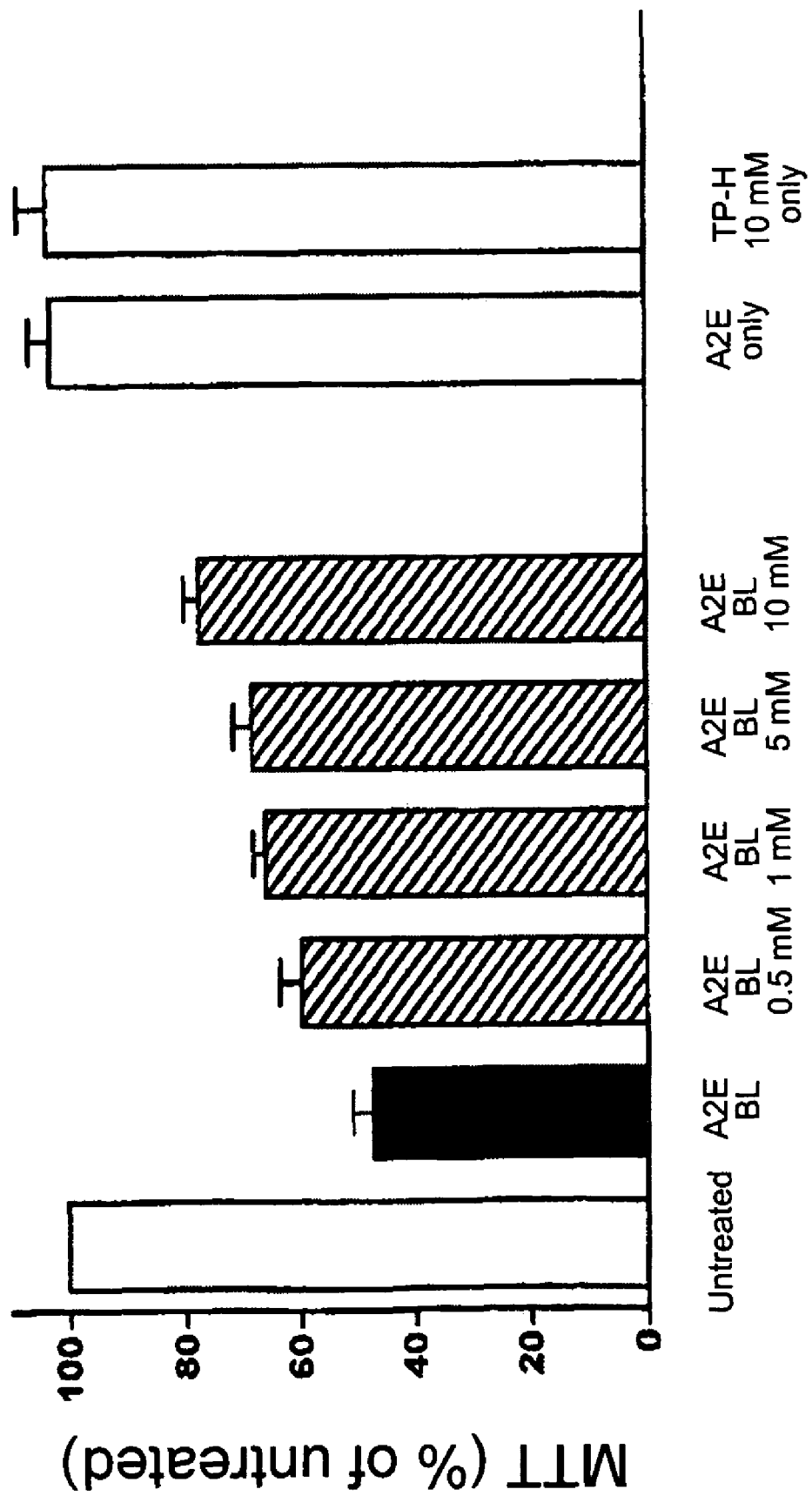
FIG. 3 shows that various concentrations of tempol-H protect blue light-illuminated A2E-laden RPE cells.
Figure 4:
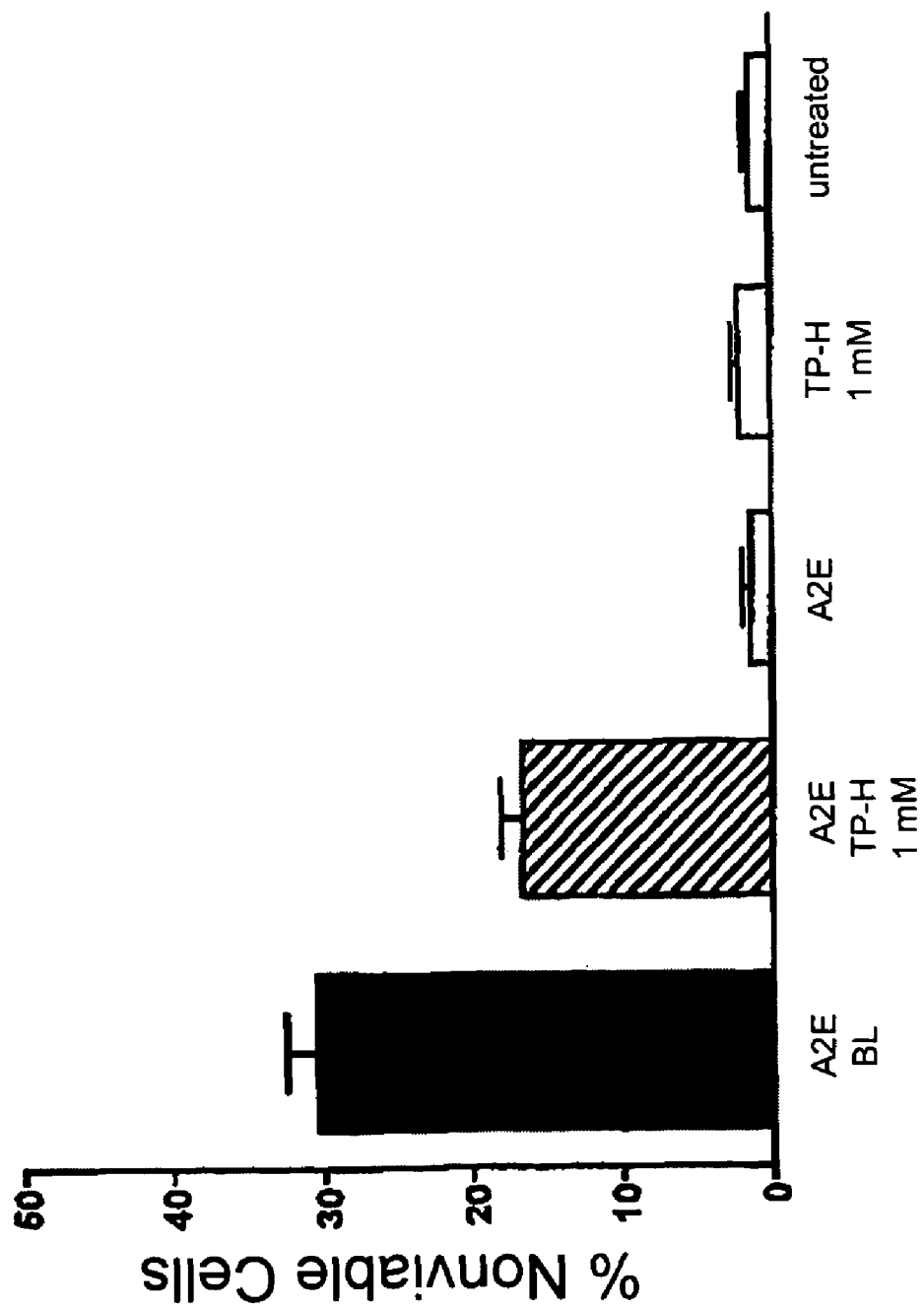
FIG. 4 shows the effect of 1 mM tempol-H in protection of blue light-illuminated A2E-laden RPE cells.

Results: As shown in FIG. 3 and FIG. 4, tempol-H affords a dose-dependent protection against the death of A2E-laden RPE in this model of macular degeneration. This represents what would be expected from Compound, I as well as tempol-H is the active metabolite of Compound I.

While the present invention has been particularly shown and described with reference to the presently preferred embodiments, it is understood that the invention is not limited to the embodiments specifically disclosed and exemplified herein. Numerous changes and modifications may be made to the preferred embodiment of the invention, and such changes and modifications may be made without departing from the scope and spirit of the invention as set forth in the appended claims.

What is claimed:

1. A method of treating macular degeneration, retinopathy, glaucoma, conjunctival diseases, eyelid disorders, corneal disease or uveitis in a patient, the method comprising topically administering to the eye of such patient a composition comprising an ophthalmically acceptable carrier or diluent containing at least one compound having the formula:

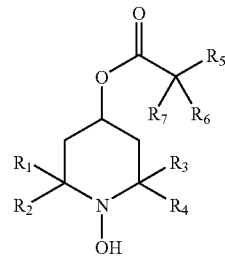

where $R_1$ and $R_2$ are, independently, H or $C_1$ to $C_3$ alkyl;
$R_3$ and $R_4$ are, independently $C_1$ to $C_3$ alkyl; and
where $R_1$ and $R_2$, taken together, or $R_3$ and $R_4$, taken together, or both may be cycloalkyl;
$R_5$ is H, OH, or $C_1$ to $C_6$ alkyl;
$R_6$ is or $C_1$ to $C_6$ alkyl, alkenyl, alkynyl, or substituted alkyl or alkenyl;
$R_7$ is $C_1$ to $C_6$ alkyl, alkenyl, alkynyl, or substituted alkyl or alkenyl
or where $R_6$ and $R_7$, or $R_5$, $R_6$ and $R_7$, taken together, form a carbocycle or heterocycle having from 3 to 7 atoms in the ring.

2. The method of claim 1 wherein $R_1$, $R_2$, $R_3$, and $R_4$ are a $C_1$-$C_3$ alkyl.

3. The method of claim 2 wherein $R_1$, $R_2$, $R_3$, and $R_4$ are ethyl groups.

4. The method of claim 2 wherein $R_1$, $R_2$, $R_3$, and $R_4$ are methyl groups.

5. The method of claim 4 wherein:
each of $R_5$ is H or methyl,
$R_6$, is methyl substituted with benzyloxy or $C_1$-$C_6$ alkoxy; and
$R_7$ is methyl.

6. The method of claim 4 wherein:
each of $R_5$ is H or methyl,
$R_6$ and $R_7$ form a cyclopropyl group.

7. The method of claim 4 wherein:
$R_5$, $R_6$ and $R_7$ form a furanyl group.

8. The method of claim 4 wherein:
$R_5$ is H; and
$R_6$ and $R_7$ form a tetrahydrofuranyl group.

9. The method of claim 4 wherein:
$R_5$ is H; and
$R_6$ and $R_7$ form a cyclopropyl ring.

10. The method of claim 1, wherein the administration is via eye drops, eye wash or eye ointment.

11. The method of claim 1 further comprising administering a reducing agent to the patient.

12. The method of claim 11, wherein the reducing agent is coadministered with the composition.

13. The method of claim 11, wherein the reducing agent is administered separately from the composition.

14. The method of claim 11 wherein the reducing agent is a sulfhydryl compound.

15. The method of claim 14 further comprising coadministering mercaptopropionyl glycine, N-acetyl cysteine, β-mercaptoethylamine, or glutathione to the patient.

16. The method of claim 11 wherein the reducing agent is administered via eye drops, eye wash or ophthalmic ointment.

17. The method of claim 1 wherein said compound is administered to achieve a concentration in the tissues and fluids of about 0.1 µM to about 10 mM.

18. The method of claim 1 wherein said compound is administered to achieve a concentration in the tissues and fluids of about 1 µM to about 5 mM.

19. The method of claim 1 wherein said compound is administered to achieve a concentration in the tissues and fluids of about 25 µM to about 1 mM.

20. The method of claim 1 wherein said compound is administered to achieve a concentration in the tissues and fluids of about 50 µM to about 100 µM.

21. The method of claim 1 wherein said disease or disorder is blepharitis.

22. The method of claim 1 wherein said disease or disorder is ocular rosacea.

23. The method of claim 1 wherein said disease or disorder is macular degeneration.

24. The method of claim 1 wherein said disease or disorder is retinopathy.

25. The method of claim 1 wherein said disease or disorder is glaucoma.

26. The method of claim 1 wherein said composition further comprises a second compound used to treat said macular degeneration, retinopathy, glaucoma, conjunctival diseases, eyelid disorders, corneal disease or uveitis.

27. The method of claim 26 wherein said second compound is administered simultaneously.

28. The method of claim 26 wherein said second compound is administered sequentially.

* * * * *